(12) United States Patent
Hayashi et al.

(10) Patent No.: US 10,413,691 B2
(45) Date of Patent: Sep. 17, 2019

(54) GAS STORAGE MASK

(71) Applicants: Hiroshima University, Hiroshima (JP); JMS Co., Ltd., Hiroshima (JP)

(72) Inventors: Yuma Hayashi, Hiroshima (JP); Atsushi Kimura, Hiroshima (JP); Noboru Saeki, Hiroshima (JP); Takashi Kondo, Hiroshima (JP); Masashi Kawamoto, Hiroshima (JP); Sachiko Otsuki, Hiroshima (JP); Kensuke Yanabe, Hiroshima (JP)

(73) Assignees: HIROSHIMA UNIVERSITY, Hirsohima (JP); JMS CO., LTD., Hiroshima (JP)

( * ) Notice: Subject to any disclaimer, the term of this patent is extended or adjusted under 35 U.S.C. 154(b) by 334 days.

(21) Appl. No.: 15/504,459

(22) PCT Filed: Aug. 19, 2015

(86) PCT No.: PCT/JP2015/073276
§ 371 (c)(1),
(2) Date: Feb. 16, 2017

(87) PCT Pub. No.: WO2016/027839
PCT Pub. Date: Feb. 25, 2016

(65) Prior Publication Data
US 2017/0232218 A1    Aug. 17, 2017

(30) Foreign Application Priority Data

Aug. 20, 2014 (JP) ................... 2014-167790
May 15, 2015 (JP) ................... 2015-100533

(51) Int. Cl.
*A61M 16/06* (2006.01)
*A41D 13/11* (2006.01)
*A62B 18/02* (2006.01)
*A61M 16/08* (2006.01)
*A61M 16/10* (2006.01)

(52) U.S. Cl.
CPC ............ *A61M 16/06* (2013.01); *A41D 13/11* (2013.01); *A61M 16/0683* (2013.01);
(Continued)

(58) Field of Classification Search
CPC .. A61M 16/00; A61M 16/06; A61M 16/0666; A61M 16/0683; A61M 16/0622;
(Continued)

(56) References Cited

U.S. PATENT DOCUMENTS 4,354,488 A   10/1982  Bartos
5,022,900 A   6/1991   Bar-Yona et al.
(Continued)

FOREIGN PATENT DOCUMENTS

GB    2267840 A    12/1993
JP    2000225191 A  8/2000
(Continued)

OTHER PUBLICATIONS

International Search Report for PCT/JP2015/073276 dated Oct. 27, 2015.

*Primary Examiner* — Manuel A Mendez
(74) *Attorney, Agent, or Firm* — Maschoff Brennan

(57) ABSTRACT

Provided is a gas storing mask which, with a simple configuration, allows a reduction in feeling of discomfort given to a patient. An oxygen delivering mask (1a) includes a first sheet (2) and a second sheet (3), oxygen supplied from outside the oxygen delivering mask (1a) being stored in a gas storing part (4) formed between the first sheet (2) and the second sheet (3).

12 Claims, 15 Drawing Sheets

(52) U.S. Cl.
CPC .... *A61M 16/0816* (2013.01); *A61M 16/0875* (2013.01); *A62B 18/02* (2013.01); *A61M 16/1065* (2014.02); *A61M 2202/0208* (2013.01)

(58) Field of Classification Search
CPC .............. A61M 16/16; A61M 16/0816; A61M 16/0875; A61M 16/1065; A61M 2202/0208; A61B 18/025; A41D 13/11; A62B 18/02
See application file for complete search history.

(56) References Cited

U.S. PATENT DOCUMENTS

| | | | |
|---|---|---|---|
| 5,165,395 A * | 11/1992 | Ricci | A41D 13/1146 128/202.22 |
| 6,196,221 B1 | 3/2001 | McCormick | |
| 6,357,440 B1 | 3/2002 | Hansen et al. | |
| 6,694,973 B1 | 2/2004 | Dunhao | |
| 6,772,759 B2 | 8/2004 | Lee | |
| 7,243,650 B2 | 7/2007 | Thornton | |
| 7,833,308 B2 | 11/2010 | Amann | |
| 2004/0132177 A1* | 7/2004 | Heron | B29C 51/14 435/297.5 |
| 2009/0188217 A1 | 7/2009 | Amann | |

FOREIGN PATENT DOCUMENTS

| | | |
|---|---|---|
| JP | 2003501220 A | 1/2003 |
| JP | 3097085 U | 1/2004 |
| JP | 2007181661 A | 7/2007 |

* cited by examiner

FIG. 15

GAS STORAGE MASK

TECHNICAL FIELD

The present invention relates to a mask in which a gas is stored. In particular, the present invention relates to an oxygen delivering mask which, with a simple structure, causes oxygen to be easily supplied to a patient and which is suitably used for a patient with a mild to moderate disease whose respiratory organ does not function normally.

BACKGROUND ART

In a case where a respiratory organ does not function normally due to a respiratory disease, a neuromuscular disease, or the like, oxygen is delivered to the nose or the mouth of a patient with use of a mask, a nasal cannula, or the like. For a patient in need of highly concentrated oxygen, a method in which a mask, a nasal cannula, or the like is used in combination of a reservoir bag is, for example, employed. For a patient in need of respiratory assistance, a method is, for example, employed in which a lung of the patient is forcibly inflated by (i) causing a mask to be in absolute contact with the nose or the mouth of the patient and (ii) carrying out positive pressure ventilation.

Such a mask or a nasal cannula is used for many hours in a state where the mask or the nasal cannula is in close or absolute contact with the mouth, the nose, or the mouth and the nose of a patient. This gives a feeling of discomfort to the patient wearing the mask or the nasal cannula. Such a feeling of discomfort is increased, as therapeutic intervention, such as (i) a method in which the mask or the nasal cannula is used in combination with a reservoir bag and (ii) a method in which positive pressure ventilation is carried out, is increased. Accordingly, oxygen delivering means, such as a mask and a nasal cannula, have been suggested which allow treatment to be efficiently provided to a patient whose respiratory organ does not function normally, while hardly giving a feeling of discomfort to the patient.

For example, Patent Literature 1 suggests the following respiratory mask in view of a conventional rigid mask shell which poorly fits the face of a person and, therefore, may cause leakage of a supplied gas or give a feeling of discomfort to the person. That is, Patent Literature 1 suggests a flexible respiratory mask including: a mask shell adapted to fit over a respiratory orifice on a portion of the face of a person, the mask shell being made of a flexible material such as a woven fabric or a non-woven fabric, the mask shell including an impermeable coating extending over at least a portion of the flexible material; a hose connector extending through the flexible material of the mask shell and fastened to the flexible material, the hose connector being a hose connector to which a gas supply hose is attached; and at least one attaching member for securing the mask shell over the portion of the face of the person. A flexible nature of the flexible material allows the respiratory mask to conform to the face of a person, regardless of the shape or the size of the face of the person. Furthermore, permeability of the flexible material allows (i) discharge of exhaled air, (ii) discharge of an excessively supplied gas and expired $CO_2$, and (iii) moisture to pass through the mask shell.

A nostril cannula is oxygen delivering means which is simple and less burdensome to a patient. However, the nostril cannula has a problem that, in a case where the nostril cannula is used outdoors, oxygen supply efficiency is decreased due to, for example, wind. In order to solve the problem, Patent Literature 2 suggests a nostril cannula substantially having a mask shape. That is, Patent Literature 2 suggests an inhalation gas supply mask including: a partition wall having a domical shape, the partition wall being brought into contact with an outer peripheral surface of an external nose of a user so as to cover the external nose; an inhalation gas introducing port via which a gas for inhalation is introduced inside the partition wall; and inhalation gas introducing means for introducing, via the inhalation gas introducing port, the gas to a space formed between (i) the wings and the tip of the nose of the user and (ii) the partition wall.

Patent Literature 3 suggests a respiratory mask for intermittently supplying positive pressure air to a user in accordance with a respiration cycle of the user. That is, Patent Literature 3 suggests a therapeutic gas introducing respiratory mask including: a positive pressure air supply port via which positive pressure air is supplied from above the nose of the user in a longitudinal direction of the nose; an exhaled air exhaust port located below the nostrils of the user; and a therapeutic gas introducing port which is provided in a vicinity of the exhaled air exhaust port and via which a therapeutic gas is introduced toward the nostrils of the user. The therapeutic gas introducing respiratory mask allows stably concentrated oxygen to be delivered to a user, and allows the user to rebreathe less exhaled air.

CITATION LIST

Patent Literature

[Patent Literature 1]
Published Japanese Translation of PCT International Application, Tokuhyo, No. 2003-501220 A (Published on Jan. 14, 2003)
[Patent Literature 2]
Japanese Patent Application Publication, Tokukai, No. 2007-181661 A (published on Jul. 19, 2007)
[Patent Literature 3]
Japanese Patent Application Publication, Tokukai, No. 2000-225191 A (published on Aug. 15, 2000)

SUMMARY OF INVENTION

Technical Problem

The therapeutic gas introducing respiratory mask disclosed on Patent Literature 3 is used in treatment in which positive pressure ventilation is carried out with use of a respiration assisting device. Out of patients whose respiratory organ does not function normally, a proportion of patients in need of such a positive pressure ventilation method is low, whereas a proportion of patients with mild to moderate diseases who are not in need of the positive pressure ventilation method is high. Under the circumstances, there is a problem that a patient with a mild to moderate disease often removes, by himself/herself, such a therapeutic mask due to a feeling of discomfort given by the therapeutic mask.

Meanwhile, in terms of an oxygen delivering function, the respiratory mask (oxygen delivering mask) disclosed in each of Patent Literatures 1 and 3, which respiratory mask allows oxygen to be delivered to the nose and the mouth of a patient, is more excellent than the nostril cannula (nasal cannula) disclosed in Patent Literature 2. That is, although an oxygen delivering mask should be provided which allows oxygen to be efficiently delivered and which hardly gives a feeling of discomfort to a patient with a mild to moderate disease, such an oxygen delivering mask has been hardly suggested.

The respiratory mask suggested by Patent Literature 1 hardly gives a feeling of discomfort to a patient with a mild to moderate disease. However, the mask shell of the respiratory mask is made of a flexible and permeable material such as a woven fabric or a non-woven fabric, and has a portion over which the impermeable coating, which is a flexible plastic, extends. This causes exhaled air, an excessively supplied gas, and moisture to be discharged through a permeable portion of the mask shell. That is, the respiratory mask is essentially a respiratory mask which is brought into absolute contact with the face of a person, and is, therefore, not necessarily a respiratory mask which hardly gives a feeling of discomfort while taking advantage of the flexible nature of the flexible material such as a woven fabric.

The present invention has been made in view of the above problems with and demands for a conventional mask, and an object of the present invention is to provide a gas storing mask which, with a simple configuration, allows a reduction in feeling of discomfort given to a patient.

Solution to Problem

In order to attain the above object, a gas storing mask in accordance with an aspect of the present invention is a gas storing mask in which a gas is stored, the gas storing mask including: a plurality of sheets, the gas, which is supplied from outside the gas storing mask, being stored in a space formed between adjacent ones of the plurality of sheets.

Advantageous Effects of Invention

According to an aspect of the present invention, a gas storing mask causes suitable humidity to be maintained between the gas storing mask and the face of a user, thereby not giving a feeling of discomfort to the user which feeling of discomfort is caused by dryness of the mouth during use of a mask. This makes it possible for the user to comfortably wear the gas storing mask for long hours and to receive, for long hours, a therapy in which the gas storing mask is used.

Figure 13:
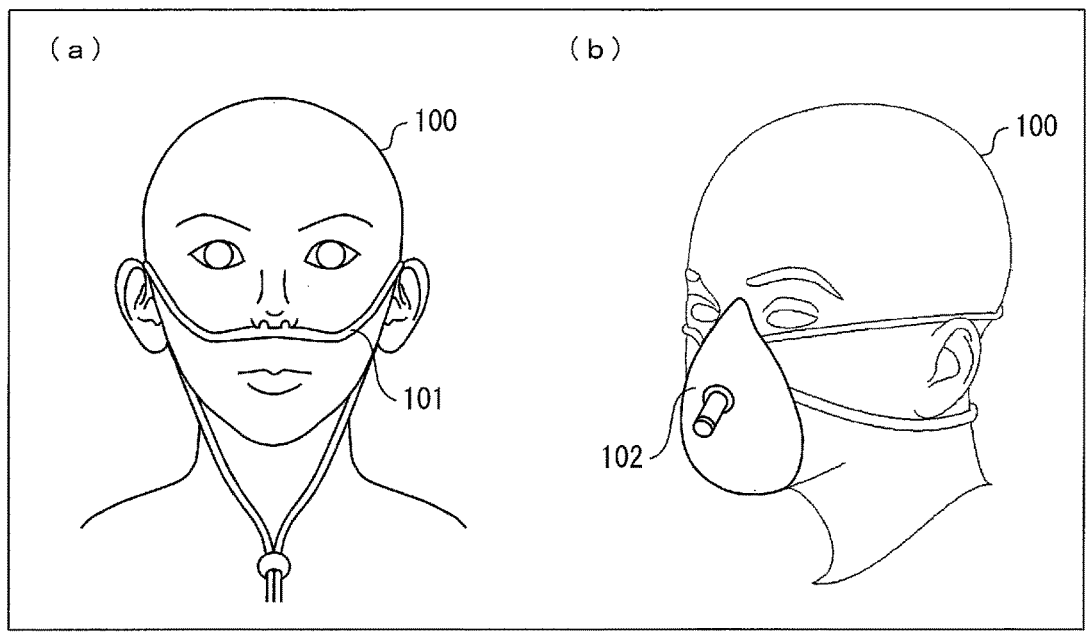

(a) of FIG. 13 is a view illustrating an example of how a nasal cannula of a conventional technique is used. (b) of FIG. 13 is a view illustrating an example of how a respiratory mask of a conventional technique is used.

Figure 14:
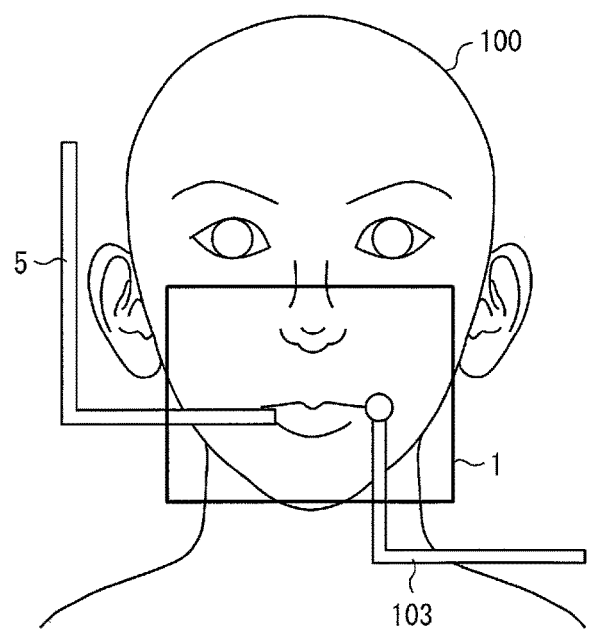

FIG. 14 is a view illustrating an outline of a test.

Figure 15:
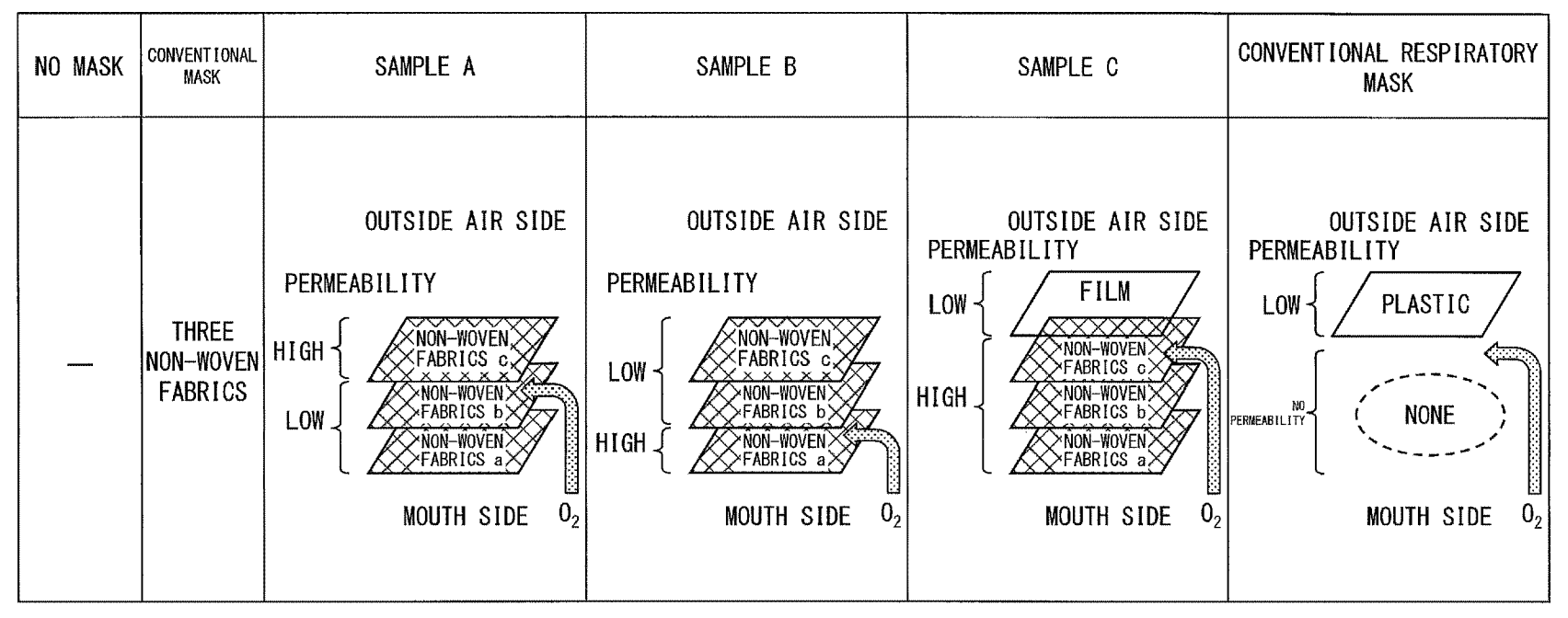

FIG. 15 is a view schematically illustrating a configuration of each of evaluation objects.

Figure 16:
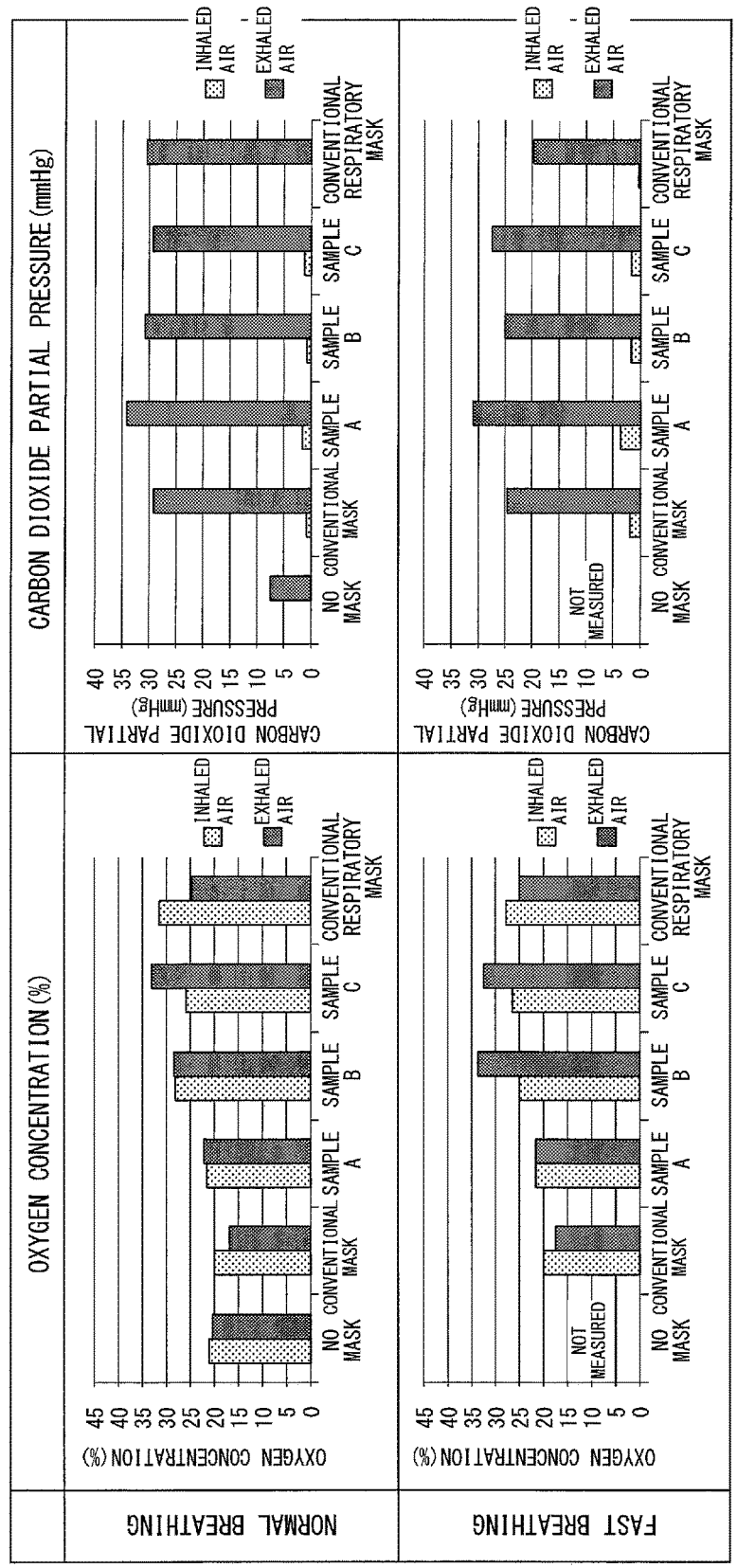

FIG. 16 is a graph showing results of measurement carried out with respect to the evaluation objects illustrated in FIG. 15.

Figure 17:
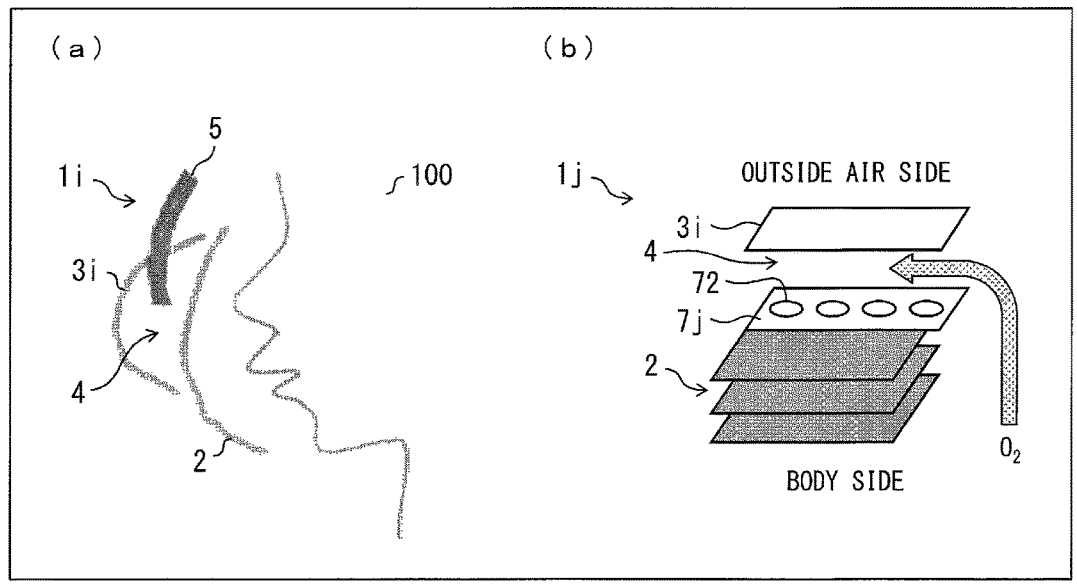

(a) of FIG. 17 is a view illustrating an example of how an oxygen delivering mask in accordance with Embodiment is worn. (b) of FIG. 17 is a view illustrating a configuration of an oxygen delivering mask which is a variation of Embodiment 9.

Figure 18:
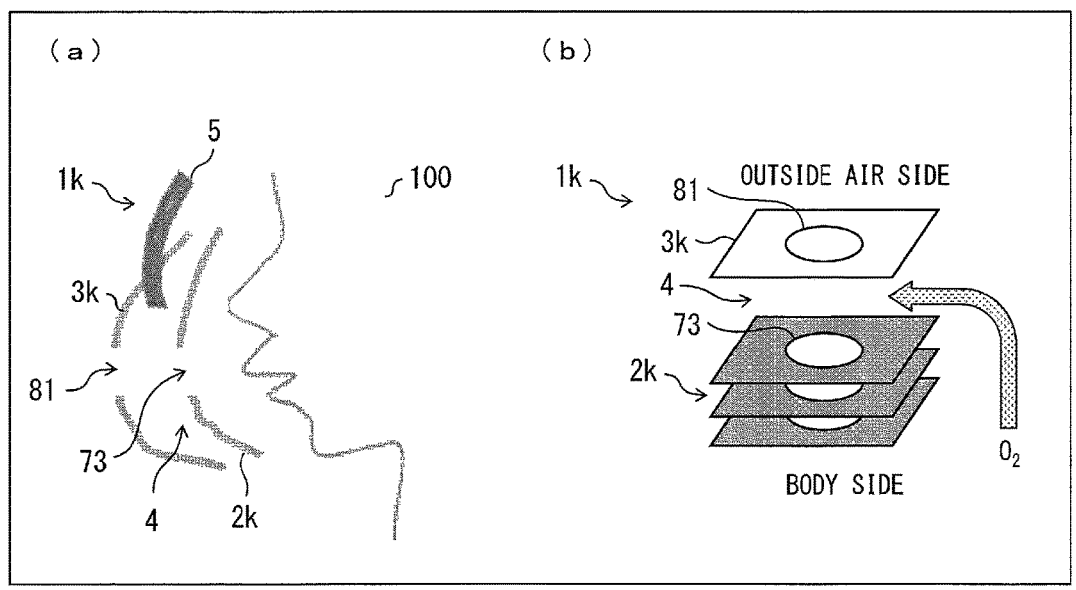

(a) of FIG. 18 is a view illustrating an example of how an oxygen delivering mask in accordance with Embodiment is worn. (b) of FIG. 18 is a view illustrating a configuration of the oxygen delivering mask.

DESCRIPTION OF EMBODIMENTS

Embodiment 1

Figure 1:
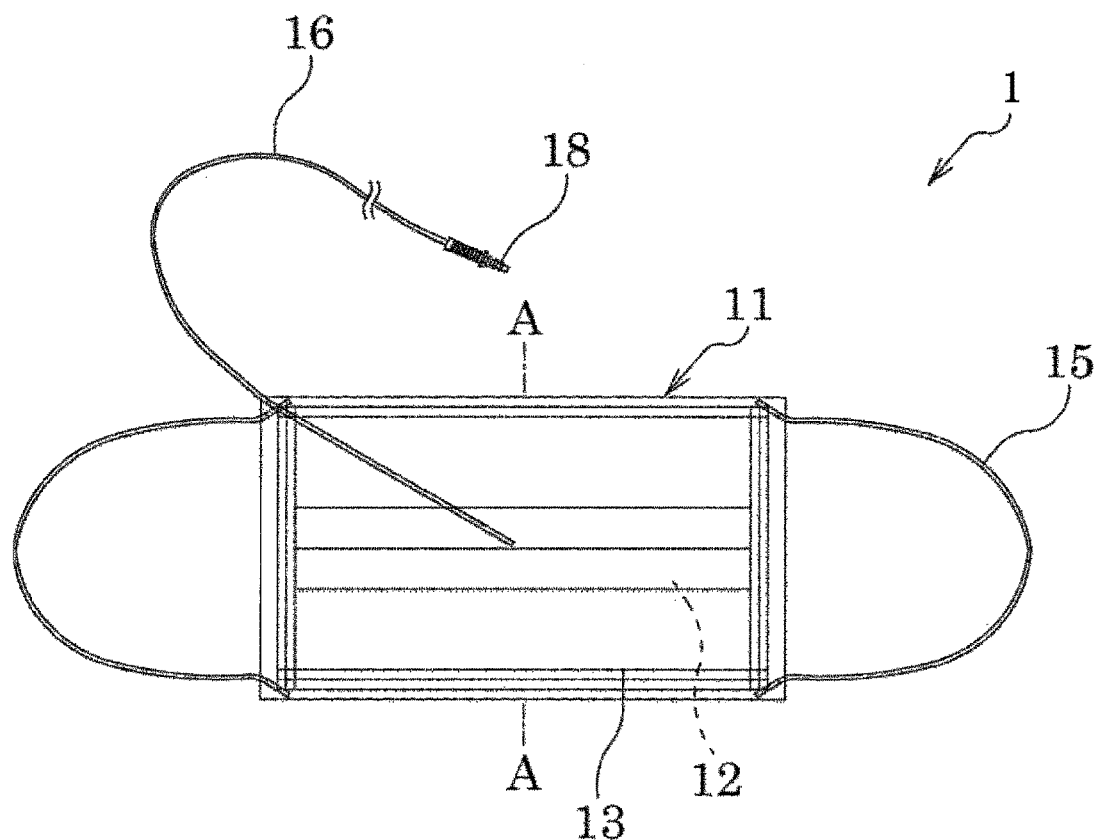
FIG. 1 is a plan view illustrating an oxygen delivering mask in accordance with the present invention.
Figure 2:
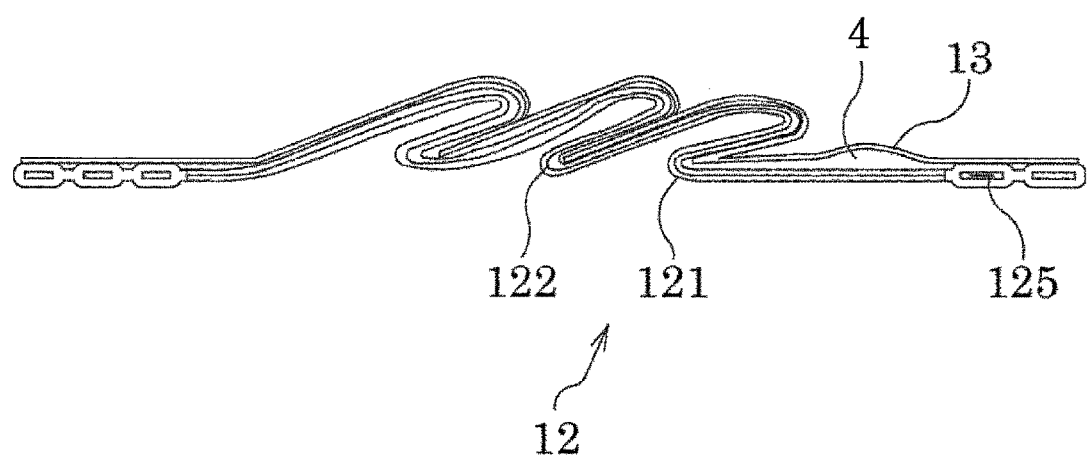
FIG. 2 is a cross-sectional view illustrating the oxygen delivering mask taken along a line A-A illustrated in FIG. 1.

The following description will discuss Embodiment 1 of the present invention with reference to the drawings. FIGS. 1 and 2 are views each schematically illustrating an oxygen delivering mask (gas storing mask) 1 in accordance with the present invention. Specifically, FIG. 1 is a plan view illustrating the oxygen delivering mask 1, and FIG. 2 is a cross-sectional view illustrating the oxygen delivering mask 1 taken along a line A-A illustrated in FIG. 1. As illustrated in FIG. 1, the oxygen delivering mask 1 in accordance with the present invention includes: a mask body 11 which includes (i) a fiber sheet (one of a plurality of sheets included in the gas storing mask, a first sheet) 12 made up of a plurality of fiber sheets which are layered on each other and (ii) a film sheet (another one of the plurality of sheets included in the gas storing mask, a second sheet) 13 covering an upper surface of the fiber sheet 12, the fiber sheet 12 and the film sheet 13 being joined together at their respective peripheral portions; an attaching part 15 which causes the mask body 11 to be attached to the body of a user; and a gas tube 16 through which an oxygen gas (gas) is delivered to a gas storing part 4 formed between the fiber sheet 12 and the film sheet 13. Note that the gas storing part 4 is formed in such a way that, by an oxygen gas (gas supplied from outside the oxygen delivering mask) delivered through the gas tube 16, a space is formed between the fiber sheet 12 and the film sheet 13 and then expanded.

Note that, in Embodiment 1 of the present invention, a fiber sheet means a sheet made by (i) weaving a resin-based fiber or a cellulose-based fiber, each of which is obtained by spinning or paper making, and (ii) melting or tangling up the resin-based fiber or the cellulose-based fiber thus woven. Examples of the fiber sheet encompass a woven fabric, a non-woven fabric, and non-woven paper. The fiber sheet 12 in accordance with Embodiment 1 is made up of such fiber sheets which are layered on each other. Specifically, the fiber sheet 12 is made up of a covering 121 and a core 122 which serve as a front surface and a back surface, respectively. The fiber sheet 12 has a band 125 which is a strengthened member and which causes (i) the oxygen delivering mask 1 to be in absolute contact with an upper portion of the nose of the user and (ii) a shape of the oxygen delivering mask 1 to be maintained. The fiber sheet 12 has adequate gaps formed by a fiber of which the fiber sheet 12 is made. This allows oxygen stored in the gas storing part 4 (later described) to be easily supplied, through the gaps formed by the fiber, to a patient wearing the oxygen delivering mask 1, and allows the oxygen stored in the gas storing part 4 to be prevented from being scattered and lost. Note that, as the fiber sheet 12, any fiber sheet which is used for a publicly known surgical mask can be employed. Note also that the band 125 can be suitably attached to a peripheral portion of the oxygen delivering mask 1. This allows an increase in strength of the oxygen delivering mask 1, and allows the oxygen delivering mask 1 to fit a patient more perfectly.

The film sheet 13 is made of a polyethylene resin, a polyvinylchloride resin, a polyamide resin, a polyethylene terephthalate resin, or the like so that the film sheet 13 can hold oxygen delivered inside the film sheet 13. The film sheet 13 is preferably transparent. In a case where the film sheet 13 of the oxygen delivering mask 1 is transparent, there is an advantage that an appearance of a patient wearing the oxygen delivering mask 1 hardly differs from an appearance of a patient wearing a surgical mask.

The fiber sheet 12 and the film sheet 13 are jointed together at their respective peripheral portions so that the fiber sheet 12 and the film sheet 13 constitute the mask body 11. The mask body 11 is provided with the gas tube 16 through which an oxygen gas is delivered between the fiber sheet 12 and the film sheet 13. The gas tube 16 has (i) a tube part joined to a corner of the mask body 11 and (ii) an end opened to a central portion of the mask body 11. This allows the gas storing part 4 to be effectively formed, and allows an oxygen gas to be efficiently supplied to a patient. The gas tube 16 extends from the mask body 11, and has a connector 18 at the other end thereof. The gas tube 16 is connected to an oxygen supply tube of an oxygen supply device (not illustrated) via the connector 18. This causes oxygen to be supplied to the gas tube 16.

In the present invention, in a case where (i) oxygen is supplied to the gas tube 16 and (ii) such an oxygen gas is delivered between the fiber sheet 12 and the film sheet 13, the fiber sheet 12 and the film sheet 13 which have been substantially layered on each other are gradually separated from each other. This ultimately causes a space to be formed between the fiber sheet 12 and the film sheet 13 and then expanded (see FIG. 2). The gas storing part 4, in which oxygen can be stored, is thus formed. That is, the gas storing part 4 is formed by expansion of the space. The oxygen delivering mask is a so-called respiratory mask having a reservoir bag.

In order to form the gas storing part 4 in which oxygen can be stored as much as possible with a simple structure, it is preferable to form the gas storing part 4 with use of the fiber sheet 12 and the film sheet 13 each of which is pleated. For example, the film sheet is arranged so as to have pleats each of which has a width greater than that of each of pleats of the fiber sheet and/or the number of which is greater than that of the pleats of the fiber sheet. By thus forming the gas storing part 4, it is possible to form a reservoir bag in which various amounts of an oxygen gas is stored with a simple structure.

The oxygen delivering mask 1 is configured such that an oxygen gas supplied from the oxygen supply device is supplied to the gas storing part 4 through the gas tube 16. Therefore, the gas tube 16 needs to (i) be easily connected to the oxygen supply device which has a given size and a given weight, (ii) be easily handed, and (ii) be good in usability. For those reasons, the gas tube 16 preferably extends from the mask body 11, and has an adequate length. For example, the gas tube 16 preferably has such a length that the connector 18, via which the gas tube 16 is connected to the oxygen supply tube of the oxygen supply device, is located behind the head of the user or below the neck of the user.

The attaching part 15 of the oxygen delivering mask 1 in accordance with Embodiment 1 takes a form of an ear loop, and is placed on an ear of the user. The attaching part 15 thus taking the form of an ear loop has the following advantage. That is, the attaching part 15 allows the user to use the oxygen delivering mask 1 as if the user used a usual surgical mask. Note, however, that the attaching part 15 can be alternatively arranged so as to be placed around the head or the neck of the user so that the oxygen delivering mask 1 is absolutely worn by the user and fixed to the user.

The oxygen delivering mask in accordance with the present invention has been described as above. A feeling which the oxygen delivering mask gives to a user wearing the oxygen delivering mask is similar to a feeling which a usual surgical mask gives to the user wearing the usual surgical mask, and the oxygen delivering mask hardly gives a feeling of discomfort to the user wearing the oxygen delivering mask. Furthermore, the oxygen delivering mask has an advantage that the oxygen delivering mask allows the user to exhale as with a case where the user exhales while wearing a usual surgical mask. Moreover, oxygen supplied while the user is exhaling is stored in the gas storing part which functions as a reservoir bag. This allows sufficient oxygen to be delivered to the user when the user inhales.

Example 1

A test was carried out so as to examine (i) an effect of an oxygen delivering mask in accordance with the present invention and (ii) a feeling which the oxygen delivering mask gives to a user wearing the oxygen delivering mask. In the test, each of 10 subjects wore an oxygen delivering mask 1 illustrated in FIG. 1, and an end-tidal oxygen concentration (%), an end-tidal carbon dioxide partial pressure (mmHg), and a degree of a feeling of discomfort (evaluated with 0 (zero) to 100 by use of a visual analog scale) which the oxygen delivering mask 1 gave to the each of the 10 subjects were measured. This measurement was carried out while (i) the each of the 10 subjects was breathing at rest and (ii) oxygen was being administered, in an amount of 3 liters per minute, to the each of the 10 subjects. The each of the 10 subjects then wore a commercially available surgical mask, and an end-tidal oxygen concentration (%), an end-tidal carbon dioxide partial pressure (mmHg), and a degree of a feeling of discomfort (evaluated with 0 (zero) to 100 by use of a visual analog scale) which the commercially available surgical mask gave to the each of the 10 subjects were similarly measured. The end-tidal oxygen concentration, the end-tidal carbon dioxide partial pressure, and the degree of the feeling of discomfort measured while the each of the 10 subjects was wearing the oxygen delivering mask 1 were compared with respective those measured while the each of the 10 subjects was wearing the commercially available surgical mask. As a statistical test, a Mann-Whitney U test was used, and $P<0.05$ was regarded as significant.

The test showed the following results. Note that numerical values coming before slash marks are numerical values obtained in a case where the each of the 10 subjects wore the oxygen delivering mask in accordance with the present invention (invention example), and numerical values coming after the slash marks are numerical values obtained in the case where the each of the 10 subjects wore the usual surgical mask (comparative example). The end-tidal oxygen concentration was 33±5%/28±3%. The end-tidal carbon dioxide partial pressure was 32±4 mmHg/30±6 mmHg. The degree of the feeling of discomfort was 14±9/34±15. The above results clearly showed an effect of the invention example. The end-tidal oxygen concentration of the invention example was 33%, whereas the end-tidal oxygen concentration of the comparative example was 28%. The degree of the feeling of discomfort of the invention example was 16, whereas the degree of the feeling of discomfort of the comparative example was 34. That is, the degree of the feeling of discomfort of the invention example was half of or less than half of the degree of the feeling of discomfort of the comparative example. It is found from those test results that the invention example (i) is excellent in feeling which a user receives and (ii) can be therefore used for long hours. Furthermore, it is found that the invention example is excellent in functional effect. Moreover, according to the above results, the oxygen delivering mask can be also used as an emergency oxygen delivering mask such as an oxygen delivering mask with which an airplane is equipped.

Embodiment 2

The following description will discuss Embodiment 2 of the present invention in detail. Note that a description of a configuration may be omitted in a case where the configuration is identical to that described in any other section below (embodiment). Note also that, for convenience, a member having a function identical to that of a member described in each section will be given an identical numerical value, and a description of the member will be omitted.

(Main Configuration)

Figure 3:
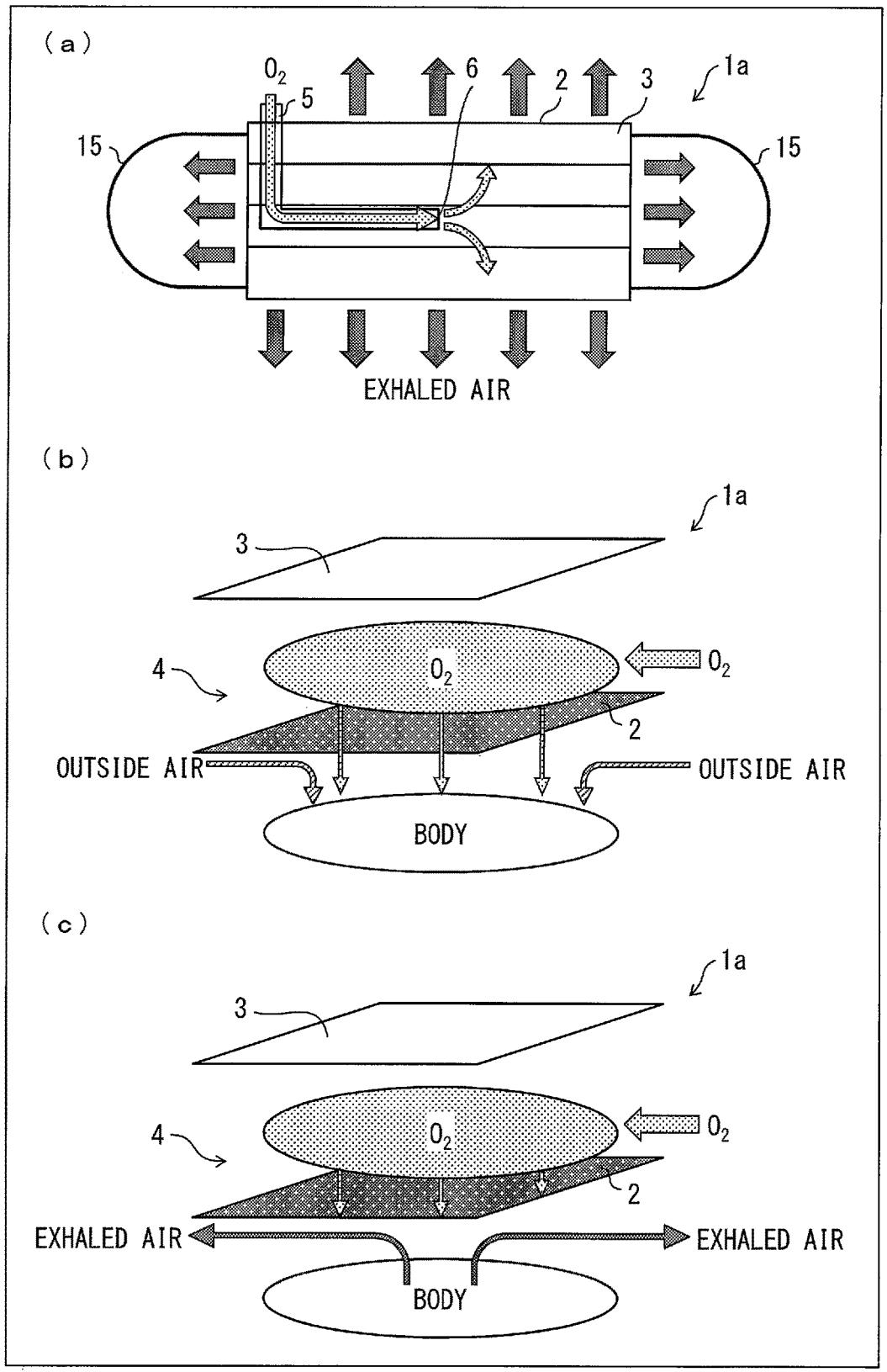
FIG. 3 is a view illustrating how a gas flows in an oxygen delivering mask in accordance with Embodiment 2.

(a) through (c) of FIG. 3 are views each illustrating how a gas flows in an oxygen delivering mask 1a in accordance with Embodiment 2. As illustrated in (b) and (c) of FIG. 3, the oxygen delivering mask (gas storing mask) 1a in accordance with Embodiment 2 includes a first sheet (one of a plurality of sheets included in the gas storing mask) 2 and a second sheet (another one of the plurality of sheets included in the gas storing mask) 3. Embodiment 2 is different from Embodiment 1 in that the first sheet 2 is not limited to the fiber sheet 12 and the second sheet 3 is not limited to the film sheet 13.

The first sheet 2 has given gas permeability. The second sheet 3 has gas permeability lower than that of the first sheet 2. Note that gas permeability means a property of an object with which property the object allows a gas to permeate the object. It is assumed that the given gas permeability of the first sheet is equal to that of a mask made of a non-woven fabric or the like.

For example, the first sheet 2 can be the fiber sheet 12. Alternatively, the first sheet 2 can be made up of a plurality of fiber sheets 12 which are layered on each other. Alternatively, the first sheet 2 can be made of a porous material. The first sheet 2 only needs to have gas permeability higher than that of the second sheet 3. Similarly, for example, the second sheet 3 can be the film sheet 13. Alternatively, the second sheet 3 can be made up of a plurality of fiber sheets 12 which are layered on each other. Alternatively, the second sheet 3 can be made up of a plurality of sheets each of which has gas permeability equal to that of the first sheet 2 and which are layered on each other.

As illustrated in (a) of FIG. 3, oxygen (gas) is supplied to the oxygen delivering mask 1a from outside the oxygen delivering mask 1a. Specifically, a gas supply pathway 5 through which a gas is supplied to the oxygen delivering mask 1a is provided between the first sheet 2 and the second sheet 3. The gas supply pathway 5 has a gas supply port 6 located at a central portion of the oxygen delivering mask 1a.

The oxygen (gas) supplied from outside the oxygen delivering mask 1a passes through the gas supply pathway 5, and is supplied, via the gas supply port 6, to the central portion of the oxygen delivering mask 1a. Air exhaled by a user wearing the oxygen delivering mask 1a is discharged outside the oxygen delivering mask 1a from a peripheral portion of the oxygen delivering mask 1a.

The Following Description Will be Given Based on a premise that a gas which passes through the gas supply pathway 5 (gas supplied from outside the oxygen delivering mask 1a) is oxygen. However, the gas is not limited to oxygen. For example, the gas which passes through the gas supply pathway 5 can be a gas containing helium or alternatively a gas containing an anesthetic or alternatively a gas containing a pharmaceutical agent necessary to treat a user.

(Flow of Gas)

How a gas flows in a case where a user inhales will be described below with reference to (b) of FIG. 3. In a case where oxygen is supplied to the oxygen delivering mask 1a, the oxygen is stored between the first sheet 2 and the second sheet 3 (stored in a space formed between adjacent ones of the plurality of sheets) as illustrated in (b) of FIG. 3. This ultimately causes a gas storing part 4 to be formed. Therefore, in a case where a user wearing the oxygen delivering mask 1a inhales, force of such user's inhalation causes the oxygen stored in the gas storing part 4 to permeate the first sheet 2 and be supplied to the body of the user.

Note that air inhaled by the user can contain air present outside the oxygen delivering mask 1a (outside air). Note also that, in a case where the user wears the oxygen delivering mask 1a, oxygen supplied via the gas supply port 6 can be stored also in a space formed between the face of the user and the oxygen delivering mask 1a (space formed between the face of the user and the plurality of sheets).

How a gas flows in a case where a user exhales will be described below with reference to (c) of FIG. 3. In a case where a user wearing the oxygen delivering mask 1a exhales, air exhaled by the user hits against the first sheet 2, and is discharged outside the oxygen delivering mask 1a through a gap between the face of the user and the oxygen delivering mask 1a.

Specifically, since oxygen continues to be supplied to the gas storing part 4, a pressure of the oxygen stored in the gas storing part 4 is increased. This causes the oxygen stored in the gas storing part 4 to intend to permeate the first sheet 2 and leak out of the gas storing part 4. Meanwhile, the air exhaled by the user is blown over the first sheet 2 from outside the gas storing part 4. In such a manner, a direction in which the oxygen stored in the gas storing part 4 applies pressure faces a direction in which the air exhaled by the user applies pressure, that is, such a direction that the air exhaled by the user applies pressure to the gas storing part 4. Therefore, the air exhaled by the user is prevented from permeating the first sheet 2 and being mixed with a gas stored in the gas storing part 4. Furthermore, the oxygen stored in the gas storing part 4 is prevented from permeating the first sheet 2 and leaking out of the gas storing part 4. Accordingly, it is possible to prevent a decrease in concentration of the oxygen stored in the gas storing part 4 which decrease is caused by the air exhaled by the user and leakage of the oxygen.

The first sheet 2 thus has the given gas permeability. Therefore, according to the oxygen delivering mask 1*a*, in a case where a user wearing the oxygen delivering mask 1*a* breathes, oxygen stored in the gas storing part 4 is easily supplied to the user when the user inhales. Furthermore, according to the oxygen delivering mask 1*a*, as has been described, air exhaled by the user does not easily enter the gas storing part 4, and the oxygen stored in the gas storing part 4 does not easily leak out of the gas storing part 4, when the user exhales.

(Humidity)

Each of the first sheet 2 and the second sheet 3 included in the oxygen delivering mask 1*a* is a flexible sheet. This causes a space to be formed between the face of a user and the oxygen delivering mask 1*a* in a case where the user wears the oxygen delivering mask 1*a*. Due to such a space, the oxygen delivering mask 1*a* does not give the user a feeling of discomfort resulting from humidity.

More specifically, most part of air exhaled by the user is discharged outside the oxygen delivering mask 1*a* as illustrated in (c) of FIG. 3, whereas some part of the air exhaled by the user remains in the space between the face of the user and the oxygen delivering mask 1*a*. Air inhaled by the user contains, as illustrated in (b) of FIG. 3, not only oxygen stored in the gas storing part 4 but also the some part of the air exhaled by the user which part remains in the space between the face of the user and the oxygen delivering mask 1*a*.

The air exhaled by the user contains more carbon dioxide than a gas stored in the gas storing part 4 does, and has higher humidity than the gas stored in the gas storing part 4 does. Therefore, the air which is inhaled by the user after exhalation and accordingly contains the some part of the air exhaled by the user can have suitable humidity. This allows the user to be prevented from having excessive dryness of the mouth due to oxygen supplied from outside the oxygen delivering mask 1*a*.

Each of the first sheet 2 and the second sheet 3 is a flexible sheet. Therefore, in a case where the user exhales, the gap is formed between the face of the user and the oxygen delivering mask 1*a*. This causes the most part of the air exhaled by the user to be discharged outside the oxygen delivering mask 1*a* through the gap. Accordingly, humidity of a gas present in the space between (i) the face of the user wearing the oxygen delivering mask 1*a* and (ii) the oxygen delivering mask 1*a* is prevented, by the user exhaling, from being excessively increased.

In this manner, it is possible for air inhaled by a user to have suitable humidity, and possible for a gas, present in a space between (i) the face of the user wearing the oxygen delivering mask 1*a* and (ii) the oxygen delivering mask 1*a*, to have suitable humidity. This ultimately allows the user to comfortably wear the oxygen delivering mask 1*a* for long hours.

(Variation of First Sheet 2)

Gas permeability of the first sheet 2 can be arranged so as to be lower on a gas storing part 4 side of the first sheet 2 than on a user side of the first sheet 2. This is realized by, for example, arranging the first sheet 2 so as to have a plurality of conical micropores. Each of the plurality of conical micropores has a diameter which becomes smaller as the each of the plurality of conical micropores extends from a first surface of the first sheet 2 which first surface is located on the gas storing part 4 side to a second surface of the first sheet 2 which second surface faces the first surface (which second surface is located on the user side).

The first sheet 2 which is arranged so as to have such a plurality of conical micropores causes (i) oxygen stored in the gas storing part 4 to easily move out of the gas storing part 4 and (ii) air exhaled by a user not to easily enter the gas storing part 4. It is therefore possible to efficiently provide, to the user, an oxygen therapy with use of the oxygen delivering mask 1*a*.

Embodiment 3

Figure 4:
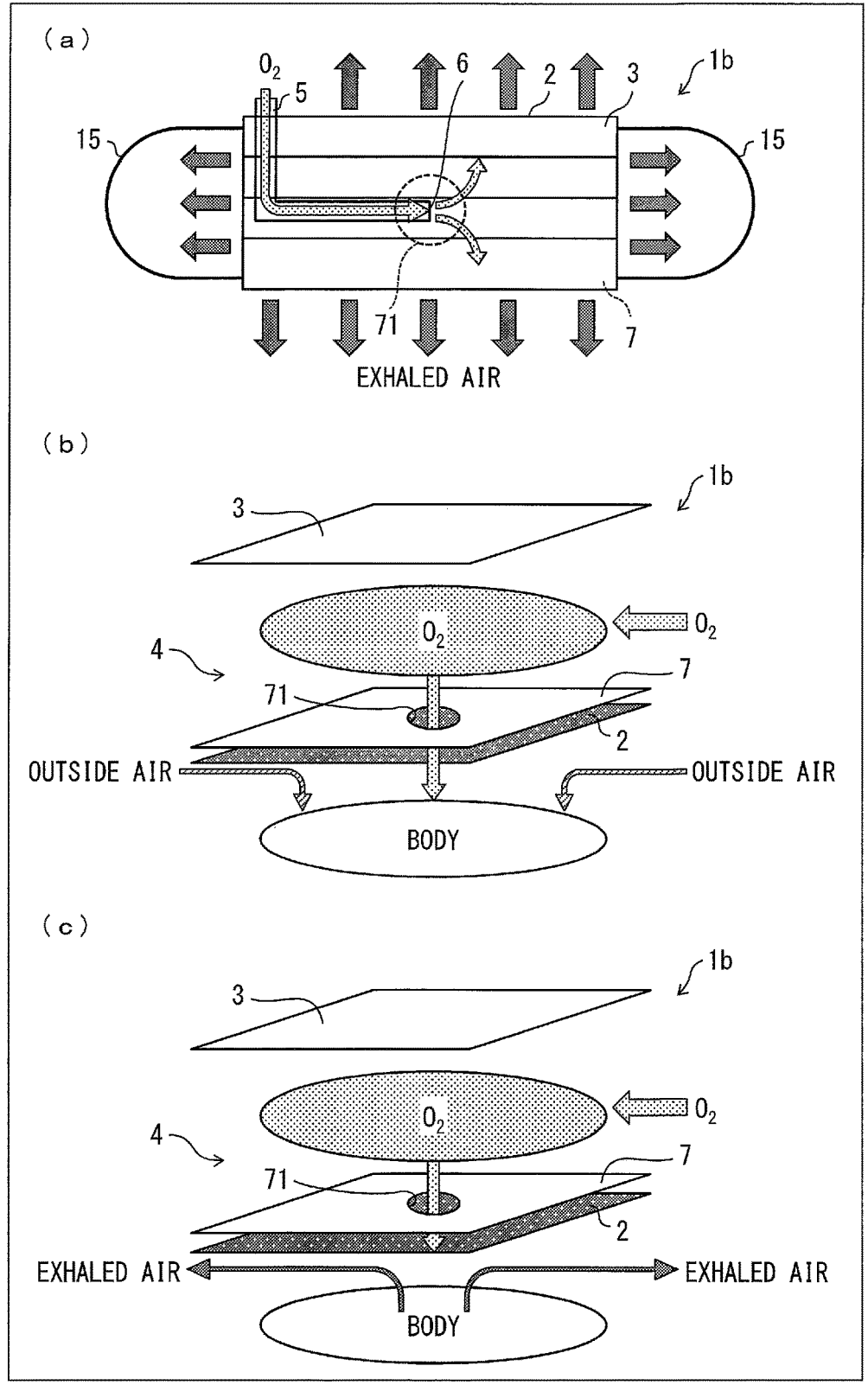
FIG. 4 is a view illustrating how a gas flows in an oxygen delivering mask in accordance with Embodiment 3.

(a) through (c) of FIG. 4 are views each illustrating how a gas flows in an oxygen delivering mask 1*b* in accordance with Embodiment 3. As illustrated in (b) and (c) of FIG. 4, the oxygen delivering mask (gas storing mask) 1*b* in accordance with Embodiment 3 further includes a third sheet 7 in addition to the configuration described in Embodiment 2. The third sheet 7 has gas permeability lower than that of a first sheet 2. For example, the third sheet 7 has gas permeability identical to that of a second sheet 3. The third sheet 7 has a hole 71.

(Main Configuration)

As illustrated in (b) of FIG. 4, the third sheet 7 is provided between the first sheet 2 and the second sheet 3. The third sheet 7 has, at a central portion thereof, the hole 71 through which oxygen (gas) stored in a gas storing part 4 is supplied to a user. A gas supply pathway 5 is provided between the second sheet 3 and the third sheet 7. The gas supply pathway 5 has a gas supply port 6 located in a vicinity of the hole 71 formed in the third sheet 7.

As illustrated in (a) of FIG. 4, oxygen passes through the gas supply pathway 5, and is supplied to the oxygen delivering mask 1*b* via the gas supply port 6. Air exhaled by a user wearing the oxygen delivering mask 1*b* is discharged outside the oxygen delivering mask 1*b* from a peripheral portion of the oxygen delivering mask 1*b*.

(Flow of Gas)

How a gas flows in a case where a user inhales will be described below with reference to (b) of FIG. 4. In a case where oxygen is supplied to the oxygen delivering mask 1*b*, the oxygen is stored between the second sheet 3 and the third sheet 7 as illustrated in (b) of FIG. 4. This ultimately causes the gas storing part 4 to be formed. Therefore, in a case where a user wearing the oxygen delivering mask 1*b* inhales, the oxygen stored in the gas storing part 4 passes through the hole 71, permeates the first sheet 2, and is supplied to the body of the user. Note that air inhaled by the user can contain not only the oxygen stored in the gas storing part 4, but also air present outside the oxygen delivering mask 1*b* (outside air).

How a gas flows in a case where a user exhales will be described below with reference to (c) of FIG. 4. In a case where a user wearing the oxygen delivering mask 1*b* exhales, air exhaled by the user hits against the first sheet 2, and is discharged outside the oxygen delivering mask 1*b*.

Specifically, since oxygen continues to be supplied to the gas storing part 4, a pressure of the oxygen stored in the gas storing part 4 is increased. This causes a gas stored in the gas storing part 4 to intend to pass through the hole 71, permeate the first sheet 2, and leak out of the gas storing part 4. Meanwhile, the air exhaled by the user is blown over the first sheet 2 from outside the gas storing part 4. In such a manner, a direction in which the oxygen stored in the gas storing part 4 applies pressure faces, in the hole 71, a direction in which the air exhaled by the user applies pressure, that is, such a direction that the air exhaled by the user applies pressure to the gas storing part 4. Therefore, the oxygen stored in the gas storing part 4 hardly leaks out of the gas storing part 4 through the hole 71.

The oxygen delivering mask 1b in accordance with Embodiment 3 is configured such that the gas storing part 4 is formed between the first sheet and the third sheet 7 which has the hole 71. Therefore, the pressure which the oxygen stored in the gas storing part 4 applies, through the hole 71, to the first sheet 2 of the oxygen delivering mask 1b in accordance with Embodiment 3 is higher than the pressure which the oxygen stored in the gas storing part 4 applies to the first sheet of the oxygen delivering mask 1a in accordance with Embodiment 2. It is therefore possible to further reduce an amount of air which is exhaled by the user and which permeates the first sheet 2, passes through the hole 71, and is mixed with the gas stored in the gas storing part 4, as compared with Embodiment 2.

Oxygen supplied via the gas supply port 6 is stored in the space formed between the third sheet 7 and the second sheet 3 each of which has gas permeability lower than that of the first sheet 2. Therefore, the oxygen stored in the gas storing part 4 is prevented from permeating the first sheet 2 and leaking out of the gas storing part 4. Furthermore, the air exhaled by the user is prevented from permeating the first sheet 2 and the third sheet 7 and being mixed with the gas stored in the gas storing part 4. It is therefore possible to prevent a decrease in concentration of the oxygen stored in the gas storing part 4 which decrease is caused by the air exhaled by the user and leakage of the oxygen.

(Variation)

The oxygen delivering mask (gas storing mask) 1b illustrated in FIG. 4 can be configured such that the first sheet 2 has at least one hole (not illustrated) through which oxygen stored in the gas storing part 4 is supplied to a user (living body). The at least one hole formed in the first sheet 2 has, for example, a shape similar to that of the hole 71 formed in the third sheet 7. Note that, in this case, the oxygen delivering mask 1b does not necessarily include the third sheet 7. Furthermore, in this case, the first sheet 2 can have any gas permeability. For example, the first sheet 2 can have gas permeability lower than that of the second sheet 3.

The first sheet 2 thus has the at least one hole. Therefore, according to this configuration, in a case where oxygen is supplied to the gas storing part 4, the oxygen is stored in the gas storing part 4, and the oxygen stored in the gas storing part 4 intends to pass through the at least one hole formed in the first sheet 2 and leak out of the gas storing part 4. Therefore, according to the oxygen delivering mask 1b, it is possible to more easily supply oxygen to a user wearing the oxygen delivering mask 1b. Moreover, a direction in which the user wearing the oxygen delivering mask 1b exhales faces a direction in which the oxygen stored in the gas storing part 4 leaks. This makes it possible to absolutely prevent air exhaled by the user from passing through the at least one hole formed in the first sheet 2 and being mixed with a gas stored in the gas storing part 4.

Embodiment 4

Figure 5:
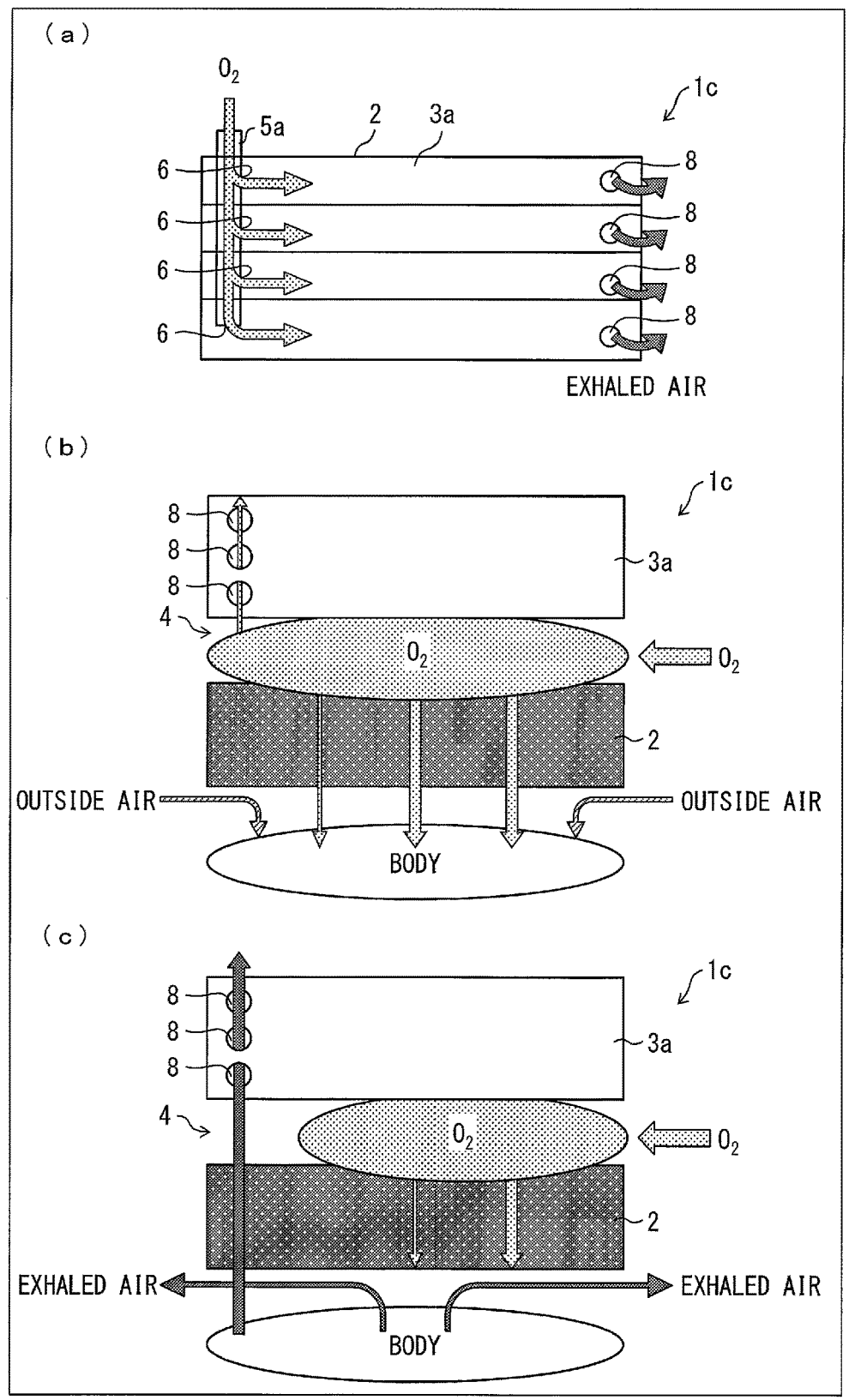
FIG. 5 is a view illustrating how a gas flows in an oxygen delivering mask in accordance with Embodiment 4.

(a) through (c) of FIG. 5 are views each illustrating how a gas flows in an oxygen delivering mask 1c in accordance with Embodiment 4. The oxygen delivering mask (gas storing mask) 1c in accordance with Embodiment 4 is different from the oxygen delivering mask 1a in accordance with Embodiment 2 in that (i) a second sheet 3a has a plurality of holes 8 and (ii) a gas supply pathway 5a has a plurality of gas supply ports 6.

(Main Configuration)

As illustrated in (a) of FIG. 5, the gas supply pathway 5a is provided between a first sheet 2 and the second sheet 3a so as to extend along a short side of the oxygen delivering mask 1c. The gas supply pathway 5a has the plurality of gas supply ports 6 at respective portions thereof which are located between the first sheet 2 and the second sheet 3a. The second sheet 3a has the plurality of holes 8 through each of which air exhaled by a user is discharged. The plurality of holes 8 are formed so as to be arranged along a short side of the oxygen delivering mask 1c which short side faces the short side along which the gas supply pathway 5a is provided so as to extend.

Oxygen which passes through the gas supply pathway 5a is supplied to the oxygen delivering mask 1c via the plurality of gas supply ports 6. Air exhaled by a user wearing the oxygen delivering mask 1c is discharged outside the oxygen delivering mask 1c through the plurality of holes 8.

(Flow of Gas)

(b) of FIG. 5 is a view illustrating how a gas flows in a case where a user inhales. In a case where oxygen is supplied to the oxygen delivering mask 1c, the oxygen is stored between the first sheet 2 and the second sheet 3a as illustrated in (b) of FIG. 5. This ultimately causes a gas storing part 4 to be formed. Therefore, in a case where a user wearing the oxygen delivering mask 1c inhales, the oxygen stored in the gas storing part 4 permeates the first sheet 2 and is supplied to the body of the user. Note that air inhaled by the user can contain not only the oxygen stored in the gas storing part 4, but also air present outside the oxygen delivering mask 1c (outside air).

(c) of FIG. 5 is a view illustrating how a gas flows in a case where a user exhales. In a case where a user wearing the oxygen delivering mask 1c exhales, some part of air exhaled by the user hits against the first sheet 2, and is discharged outside the oxygen delivering mask 1c. Meanwhile, some part of the air exhaled by the user permeates the first sheet 2, enters the gas storing part 4, passes through the plurality of holes 8, and is then discharged outside the oxygen delivering mask 1c. Therefore, an amount of air which is exhaled by the user and which is discharged outside the oxygen delivering mask 1c is larger than those in Embodiments 2 and 3. This makes it possible to suppress an increase in concentration of carbon dioxide in the oxygen delivering mask 1c.

As illustrated in (c) of FIG. 5, some part of the air exhaled by the user permeates the first sheet 2, passes through the plurality of holes 8 formed in the second sheet 3a, and is then discharged outside the gas storing part 4. Such a flow of the some part of the air exhaled by the user causes a gas stored in the gas storing part 4 to flow from a portion of the gas storing part 4 which portion is closer to the plurality of holes 8 to a portion of the gas storing part 4 which portion is farther from the plurality of holes 8. This causes the gas stored in the gas storing part 4 not to easily leak out of the gas storing part 4 through the plurality of holes 8. Therefore, it is possible to prevent concentration of oxygen, contained in the gas stored in the gas storing part 4, from decreasing in a case where the user exhales.

(Variation)

Figure 6:
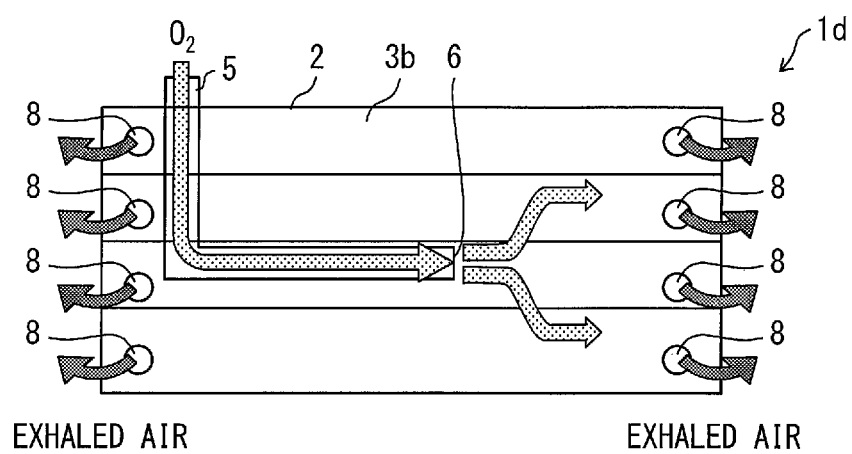
FIG. 6 is a view illustrating a variation of the oxygen delivering mask in accordance with Embodiment 4.

Next, a variation of Embodiment 4 will be described below. FIG. 6 is a view illustrating an outline of how a gas flows in an oxygen delivering mask (gas storing mask) 1d. The oxygen delivering mask 1d is different from the oxygen delivering mask 1c in accordance with Embodiment 4 in that a second sheet 3b has a plurality of holes 8 along each of two short sides of the second sheet 3b which two short sides faces each other. Further, a gas supply pathway 5 has a gas supply port 6 at an end of the gas supply pathway 5. The gas supply port 6 is located at a central portion of the oxygen delivering mask 1*d*.

As illustrated in FIG. 6, oxygen which passes through the gas supply pathway 5 is supplied to the oxygen delivering mask 1*d* via the gas supply port 6. Air exhaled by a user wearing the oxygen delivering mask 1*d* is discharged outside the oxygen delivering mask 1*d* through the plurality of holes 8 formed so as to be arranged along each of two sides of the oxygen delivering mask 1*d*. Therefore, an amount of air which is exhaled by the user and which is discharged outside the oxygen delivering mask 1*d* is large, as compared with the oxygen delivering mask 1*c* illustrated in (a) of FIG. 5. This makes it possible to prevent an increase in concentration of carbon dioxide in the oxygen delivering mask 1*d*.

Embodiment 5

Figure 7:
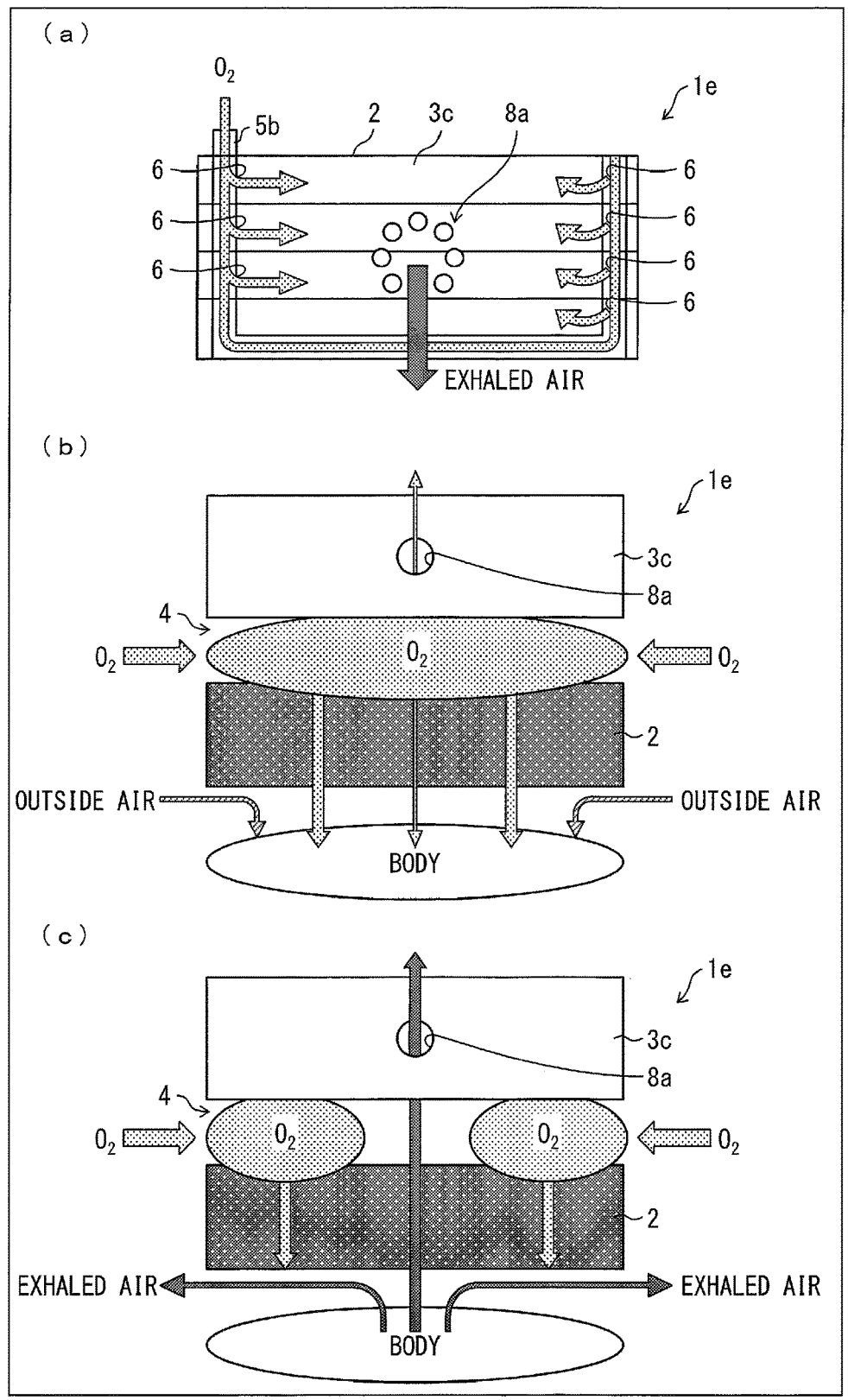
FIG. 7 is a view illustrating how a gas flows in an oxygen delivering mask in accordance with Embodiment 5.

(a) through (c) of FIG. 7 are views each illustrating how a gas flows in an oxygen delivering mask (gas storing mask) 1*e* in accordance with Embodiment 5. The oxygen delivering mask 1*e* in accordance with Embodiment 5 is different from the oxygen delivering mask 1*c* in accordance with Embodiment 4 in that a second sheet 3*c* has, at a central portion thereof, holes 8*a* through each of which air exhaled by a user is discharged.

(Main Configuration)

As illustrated in (a) of FIG. 7, the second sheet 3*c* has a plurality of micropores serving as the respective holes 8*a*. A gas supply pathway 5*b* is provided between a first sheet 2 and the second sheet 3*c* so as to extend along three sides, that is, a short side, a long side, and a short side of the oxygen delivering mask 1*e*. The gas supply pathway 5*b* provided between the first sheet 2 and the second sheet 3*c* has a plurality of gas supply ports 6 at respective portions thereof which are located along such short sides, facing each other, of the oxygen delivering mask 1*e*.

Oxygen which passes through the gas supply pathway 5*b* is supplied to a central portion of the oxygen delivering mask 1*e* from the short sides of the oxygen delivering mask 1*e* via the plurality of gas supply ports 6. Air exhaled by a user wearing the oxygen delivering mask 1*e* is discharged outside the oxygen delivering mask 1*e* through the holes 8*a* formed so as to be arranged at the central portion of the oxygen delivering mask 1*e*. Note that (b) and (c) of FIG. 7 each illustrate the holes 8*a* as a single hole, although the holes 8*a* are a plurality of micropores.

(Flow of Gas)

(b) of FIG. 7 is a view illustrating how a gas flows in a case where a user inhales. In a case where oxygen is supplied to the oxygen delivering mask 1*e*, the oxygen is stored between the first sheet 2 and the second sheet 3*c* as illustrated in (b) of FIG. 7. This ultimately causes a gas storing part 4 to be formed. Therefore, in a case where a user wearing the oxygen delivering mask 1*e* inhales, the oxygen stored in the gas storing part 4 permeates the first sheet 2 and is supplied to the body of the user. Note that air inhaled by the user can contain not only the oxygen stored in the gas storing part 4, but also air present outside the oxygen delivering mask 1*e* (outside air).

(c) of FIG. 7 is a view illustrating how a gas flows in a case where a user exhales. In a case where a user wearing the oxygen delivering mask 1*e* exhales, some part of air exhaled by the user hits against the first sheet 2, and is discharged outside the oxygen delivering mask 1*e*. Note that the holes 8*a* are formed in the central portion of the second sheet 3*c*. Therefore, some part of the air exhaled by the user permeates the first sheet 2 due to force of such user's exhalation, enters the gas storing part 4, and passes through the holes 8*a*, and is then discharged outside the oxygen delivering mask 1*e*. It is therefore possible to prevent concentration of carbon dioxide in the oxygen delivering mask 1*e* from increasing in a case where a user exhales.

As illustrated in (c) of FIG. 7, some part of the air exhaled by the user permeates the first sheet 2, passes through the plurality of holes 8*a*, and is the discharged outside the gas storing part 4. Such a flow of the some part of the air exhaled by the user causes a gas stored in the gas storing part 4 to flow so as to be away from the holes 8*a*. This causes the gas stored in the gas storing part 4 not to leak out of the gas storing part 4 through the holes 8*a*. Therefore, it is possible to prevent concentration of oxygen, contained in the gas stored in the gas storing part 4*a*, from decreasing in a case where the user exhales.

The holes 8*a* formed in the second sheet 3*c* are micropores. Therefore, as illustrated in (b) of FIG. 7, it is possible to minimize an amount of the gas which passes through the holes 8*a* and leaks out of the gas storing part 4, in a case where the user inhales. This ultimately makes it possible to prevent concentration of oxygen, contained in the gas stored in the gas storing part 4, from decreasing in a case where the user inhales. Furthermore, in a case where the oxygen delivering mask 1*e* is worn by a user in such a way that the second sheet 3*c* having the holes 8*a*, which are micropores, faces outside, a feeling of strangeness in appearance is reduced. This allows the user to wear the oxygen delivering mask 1*e* without worrying about the public eye, as with the case of a conventional surgical mask.

Embodiment 6

Figure 8:
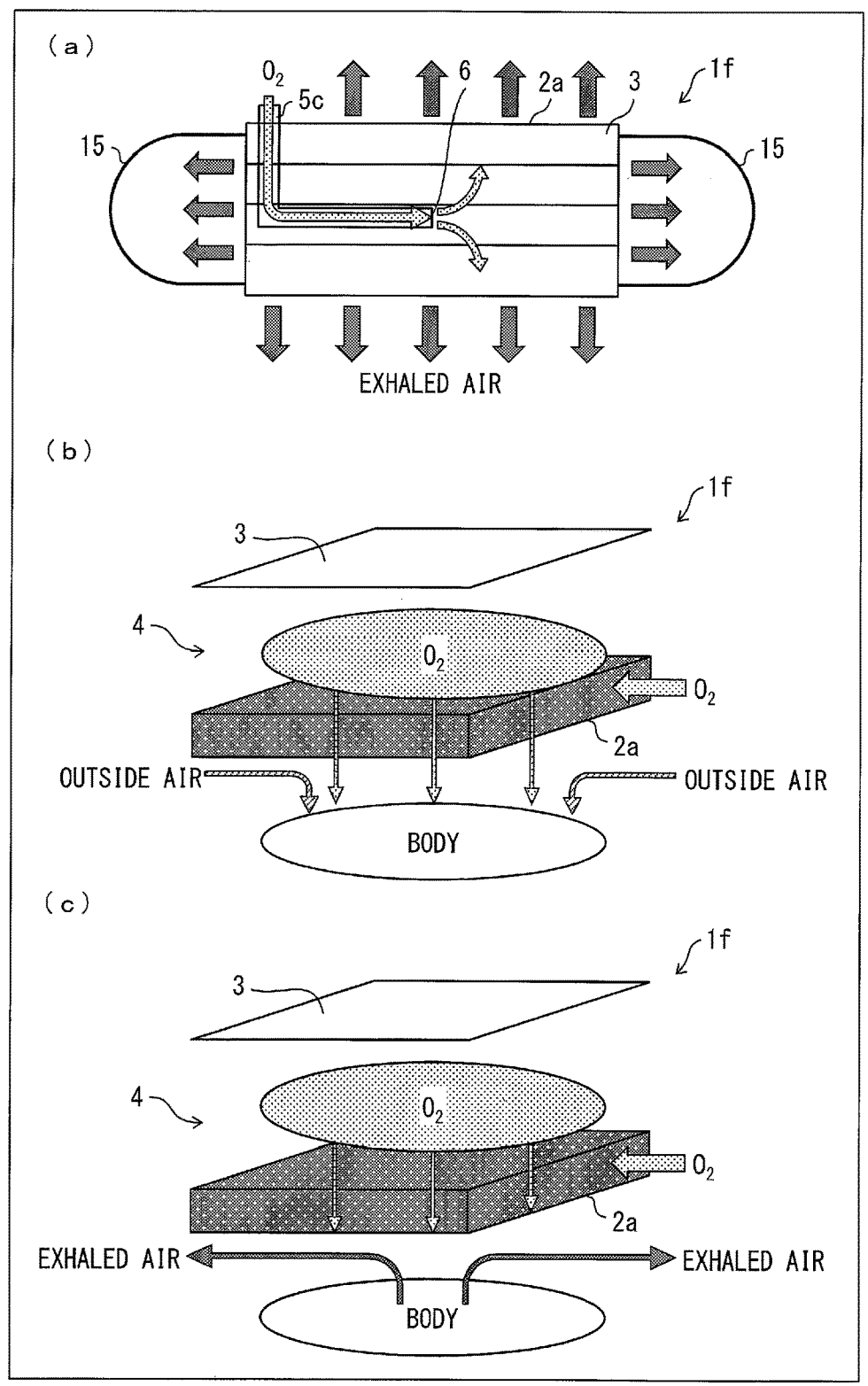
FIG. 8 is a view illustrating how a gas flows in an oxygen delivering mask in accordance with Embodiment 6.

(a) through (c) of FIG. 8 are views each illustrating how a gas flows in an oxygen delivering mask 1*f* in accordance with Embodiment 6. The oxygen delivering mask 1*f* in accordance with Embodiment 6 is different from the oxygen delivering mask 1*a* in accordance with Embodiment 2 in that a gas supply pathway 5*c* is not necessarily provided between a first sheet 2*a* and a second sheet 3.

(Main Configuration)

As illustrated in (b) of FIG. 8, the oxygen delivering mask (gas storing mask) 1*f* includes a first sheet 2*a* having a thickness greater than that of the first sheet 2 of Embodiment 2. A gas supply port 6 is located so that oxygen which passes through a gas supply pathway 5*c* is supplied to the first sheet 2*a*. The gas supply pathway 5*c* can be provided, for example, on a side surface of the first sheet 2*a* or can be alternatively provided inside the first sheet 2*a*. The gas supply port 6 can be located, for example, so that oxygen is supplied in a direction perpendicular to a thickness direction of the first sheet 2*a*.

As illustrated in (a) of FIG. 8, oxygen supplied from outside the oxygen delivering mask 1*e* passes through the gas supply pathway 5*c*, and is supplied to a central portion of the oxygen delivering mask 1*f* via the gas supply port 6. Air exhaled by a user wearing the oxygen delivering mask 1*f* is discharged outside the oxygen delivering mask 1*f* from a peripheral portion of the oxygen delivering mask 1*f*.

(Flow of Gas)

How a gas flows in a case where a user inhales will be described below with reference to (b) of FIG. 8. As illustrated in (b) of FIG. 8, oxygen is supplied to the first sheet 2*a* from outside the oxygen delivering mask 1*f*, and most part of the oxygen thus supplied permeates the first sheet 2*a* and is stored between the first sheet 2a and the second sheet 3. This ultimately causes a gas storing part 4 to be formed. Note that, since the first sheet 2a is thick, some part of the oxygen supplied from outside the oxygen delivering mask 1f is contained in the first sheet 2a.

In a case where a user wearing the oxygen delivering mask 1f inhales, the most part of the oxygen, which part is stored in the gas storing part 4, and the some part of the oxygen, which part is contained in the first sheet 2a, permeate the first sheet 2a, and are supplied to the body of the user.

How a gas flows in a case where a user exhales will be described below with reference to (c) of FIG. 8. In a case where a user wearing the oxygen delivering mask 1f exhales, air exhaled by the user hits against the first sheet 2a, and is discharged outside the oxygen delivering mask 1f. In a case where the user exhales, a direction in which the most part of the oxygen, which part is stored in the gas storing part 4, applies pressure faces a direction in which the air exhaled by the user applies pressure, that is, such a direction that the air exhaled by the user applies pressure to the gas storing part 4. Furthermore, the first sheet 2a is thick. Therefore, the air exhaled by the user is prevented from permeating the first sheet 2a and being mixed with a gas stored in the gas storing part 4.

Embodiment 7

Figure 9:
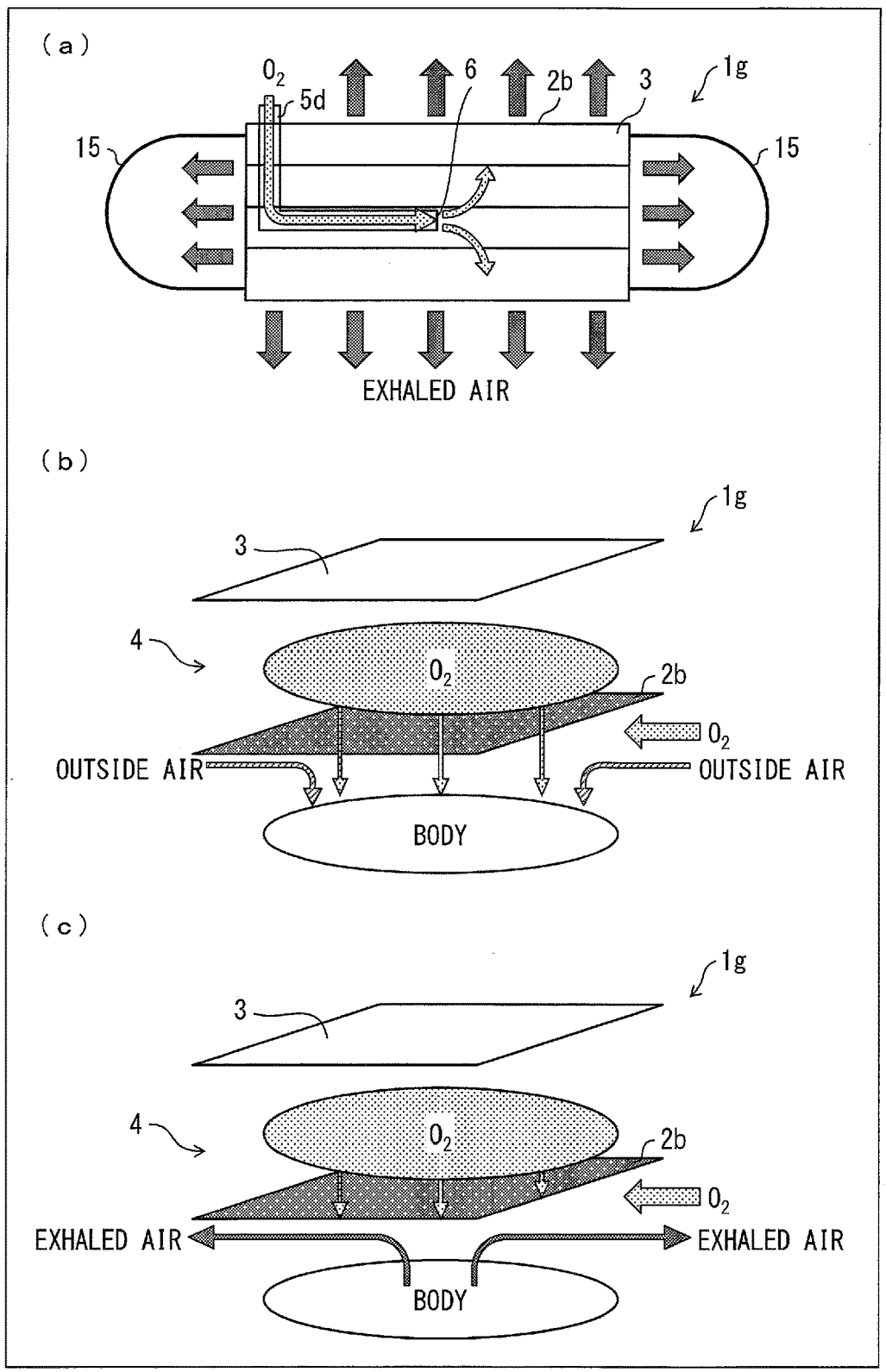
FIG. 9 is a view illustrating how a gas flows in an oxygen delivering mask in accordance with Embodiment 7.

(a) through (c) of FIG. 9 are views each illustrating how a gas flows in an oxygen delivering mask (gas storing mask) 1g in accordance with Embodiment 7. The oxygen delivering mask 1g in accordance with Embodiment 7 is different from the oxygen delivering mask 1a in accordance with Embodiment 2 in that a gas supply pathway 5d is not necessarily provided between a first sheet 2b and a second sheet 3.

According to Embodiment 7, the gas supply pathway 5d is provided outside the oxygen delivering mask 1g. A gas supply port 6 is located on an outer side of the first sheet 2b, that is, located on an outer side of the oxygen delivering mask 1g. Specifically, the gas supply port 6 is located between the first sheet 2b and the face of a user wearing the oxygen delivering mask 1g. Providing the gas supply pathway 5d to the oxygen delivering mask 1g in such a way is easier than providing the gas supply pathway 5d between the first sheet 2b and the second sheet 3.

Oxygen supplied via the gas supply port 6 permeates the first sheet 2b, and is stored between the first sheet 2b and the second sheet 3 (stored in a space formed between adjacent ones of the plurality of sheets). This ultimately causes a gas storing part 4 to be formed. In a case where a user wears the oxygen delivering mask 1g, part of the oxygen supplied via the gas supply port 6 is stored also in a space between the face of the user and the oxygen delivering mask 1g (space formed between the face of the user and the plurality of sheets). Air exhaled by the user wearing the oxygen delivering mask 1g is discharged outside the oxygen delivering mask 1g from a peripheral portion of the oxygen delivering mask 1g.

(Flow of Gas)

How a gas flows in a case where a user inhales will be described below with reference to (b) of FIG. 9. As illustrated in (b) of FIG. 9, in a case where a user wearing the oxygen delivering mask 1g inhales, oxygen stored in the gas storing part 4 permeates the first sheet 2b and is supplied to the body of the user. Simultaneously, oxygen being supplied via the gas supply port 6 is also supplied to the body of the user.

How a gas flows in a case where a user exhales will be described below with reference to (c) of FIG. 9. In a case where a user wearing the oxygen delivering mask 1g exhales, air exhaled by the user hits against the first sheet 2b, and is discharged outside the oxygen delivering mask 1g. In a case where the user exhales, a direction in which the oxygen stored in the gas storing part 4 applies pressure faces a direction in which the air exhaled by the user applies pressure, that is, such a direction that the air exhaled by the user applies pressure to the gas storing part 4. Therefore, the air exhaled by the user is prevented from permeating the first sheet 2a and being mixed with a gas stored in the gas storing part 4.

Embodiment 8

Figure 10:
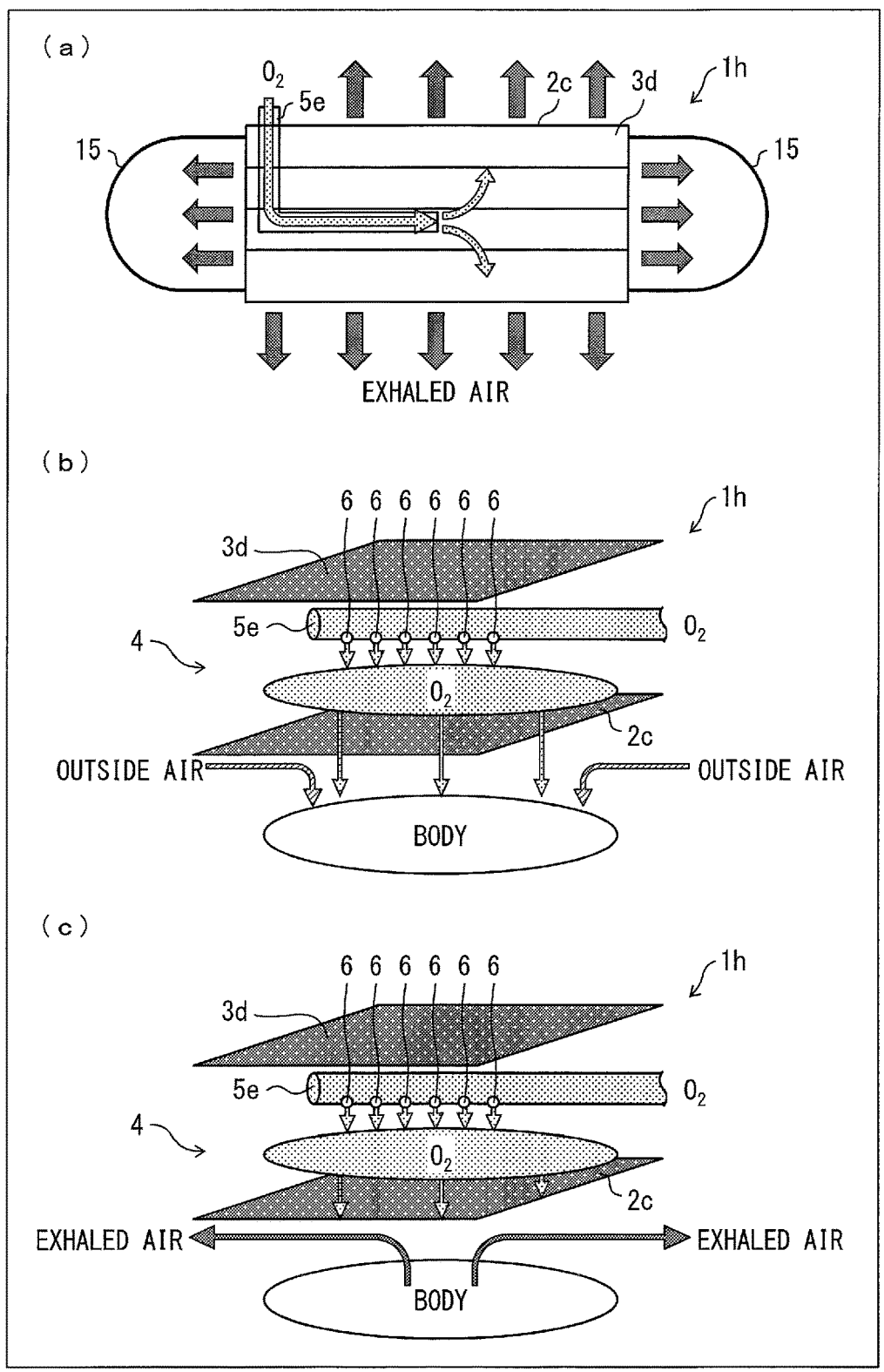
FIG. 10 is a view illustrating how a gas flows in an oxygen delivering mask in accordance with Embodiment 8.

(a) through (c) of FIG. 10 are views each illustrating how a gas flows in an oxygen delivering mask (gas storing mask) 1h in accordance with Embodiment 8. The oxygen delivering mask 1h in accordance with Embodiment 8 is different from the oxygen delivering mask 1a in accordance with Embodiment 2 in that a first sheet 2c and a second sheet 3d are not necessarily different from each other in gas permeability.

(Main Configuration)

The oxygen delivering mask 1h in accordance with Embodiment 8 includes the first sheet 2c and the second sheet 3d which are identical to each other in gas permeability. As illustrated in (b) of FIG. 10, a gas supply pathway 5e is provided between the first sheet 2c and the second sheet 3d. The gas supply pathway 5e has a plurality of gas supply ports 6 which are formed in a line so as to face the first sheet 2c. That is, the plurality of gas supply ports 6 are located so that oxygen is emitted toward the first sheet 2c.

Note that the gas permeability of the second sheet 3d is not limited in particular, provided that the plurality of gas supply ports 6 are formed, in a line, in the gas supply pathway 5e so as to face the first sheet 2c. For example, the second sheet 3d can have gas permeability higher than that of the first sheet 2c.

As illustrated in (a) of FIG. 10, oxygen supplied from outside the oxygen delivering mask 1h passes through the gas supply pathway 5e, and is supplied to a central portion of the oxygen delivering mask 1h via the plurality of gas supply ports 6. Air exhaled by a user wearing the oxygen delivering mask 1h is discharged outside the oxygen delivering mask 1h from a peripheral portion of the oxygen delivering mask 1h.

(Flow of Gas)

How a gas flows in a case where a user inhales will be described below with reference to (b) of FIG. 10. In a case where oxygen is supplied to the oxygen delivering mask 1h via the plurality of gas supply ports 6, the oxygen is stored between the first sheet 2c and the second sheet 3d as illustrated in (b) of FIG. 10. This ultimately causes a gas storing part 4 to be formed. In a case where a user wearing the oxygen delivering mask 1h inhales, the oxygen stored in the gas storing part 4 permeates the first sheet 2c, and is supplied to the body of the user. Note that air inhaled by the user can contain not only the oxygen stored in the gas storing part 4, but also air present outside the oxygen delivering mask 1h (outside air).

As illustrated in (b) of FIG. 10, a gas supplied via the plurality of gas supply ports 6 is emitted toward the first sheet 2c. This causes the gas to permeate the first sheet 2c more easily than the gas permeates the second sheet 3d. For example, even in a case where the second sheet 3d has gas permeability higher than that of the first sheet 2c, a gas supplied via the plurality of gas supply ports 6 permeates the first sheet 2c more easily than the gas permeates the second sheet 3d.

How a gas flows in a case where a user exhales will be described below with reference to (c) of FIG. 10. In a case where a user wearing the oxygen delivering mask 1h exhales, air exhaled by the user hits against the first sheet 2c, and is discharged outside the oxygen delivering mask 1h. In a case of a configuration described in Embodiment 8, a direction in which the oxygen supplied via the plurality of gas supply ports 6 is emitted and a direction in which the oxygen stored in the gas storing part 4 applies pressure each face a direction in which the air exhaled by the user applies pressure, that is, such a direction that the air exhaled by the user applies pressure to the gas storing part 4. Therefore, the air exhaled by the user is prevented from permeating the first sheet 2c and being mixed with a gas stored in the gas storing part 4. Accordingly, it is possible to prevent a decrease in concentration of the oxygen stored in the gas storing part 4 which decrease is caused by the air exhaled by the user.

[Location of Gas Supply Port]

Figure 11:
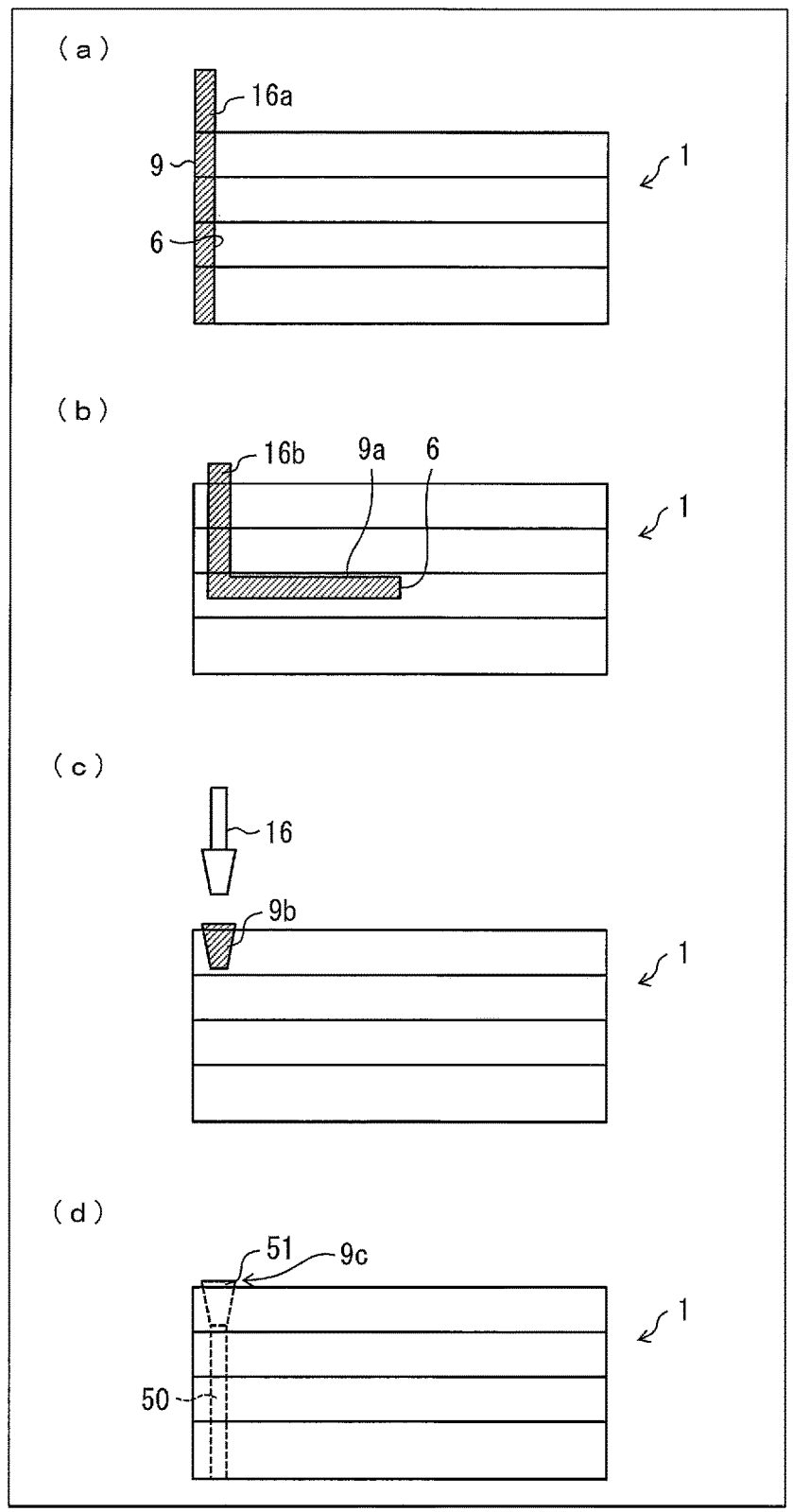
FIG. 11 is a view illustrating a connecting part via which a gas supply port of a gas supply pathway is connected to an oxygen delivering mask.

(a) through (d) of FIG. 11 are views each illustrating a connecting part via which a gas supply port(s) 6 of a gas supply pathway 5, 5a through 5e in Embodiments 1 through 8 is/are connected to an oxygen delivering mask 1.

(a) of FIG. 11 is a view illustrating a configuration in which a tube 16a (gas tube) is adhered, as a gas supply pathway, to an oxygen delivering mask 1. As illustrated in (a) of FIG. 11, the tube 16a is adhered to the oxygen delivering mask 1 so as to extend along a short side of the oxygen delivering mask 1. In a case of this configuration, a connecting part 9 via which a gas supply port 6 is connected to the oxygen delivering mask 1 is an adhesive member which causes the tube 16a to be adhered to the oxygen delivering mask 1. Note that the tube 16a is a tube through which oxygen is supplied from an oxygen supply device, and the tube 16a can be the gas tube 16 illustrated in FIG. 1.

For example, in a case of Embodiment 4, the tube 16a is adhered to at least one of the first sheet 2 and the second sheet 3a, between which the gas storing part 4 is formed, so as to be located between the first sheet 2 and the second sheet 3a (see FIG. 5). Note that a plurality of gas supply ports 6 can be alternatively formed in respective portions of the tube 16a which portions are adhered to the oxygen delivering mask 1.

According to the above configuration, since the tube 16a is connected to the oxygen delivering mask 1 so as to extend along the short side of the oxygen delivering mask 1, the tube 16a is not easily noticeable in appearance in a case where a user wears the oxygen delivering mask 1. This allows the user to wear the oxygen delivering mask 1 without worrying about the public eye, as with the case of a conventional surgical mask.

Furthermore, since the tube 16a is adhered to the oxygen delivering mask 1, the user does not need to (i) set the gas supply pathway to the oxygen delivering mask 1, (ii) position the gas supply port 6 of the gas supply pathway, and (iii) connect the gas supply port 6 to the oxygen delivering mask 1, in a case where the user uses the oxygen delivering mask 1.

(b) of FIG. 11 is a variation of the configuration illustrated in (a) of FIG. 11. A tube (gas tube) 16b illustrated in (b) of FIG. 11 has an L shape. Part of the tube 16b is adhered to an oxygen delivering mask 1 so as to extend along a short side of the oxygen delivering mask 1, and other part of the tube 16b is adhered to the oxygen delivering mask 1 so as to extend toward a central portion of the oxygen delivering mask 1 so that an end of the tube 16b is located at the central portion of the oxygen delivering mask 1. Note that a gas supply port(s) 6 is/are formed in the other part of the tube 16b. Note also that the part of the tube 16b, which part is adhered to the oxygen delivering mask 1 so as to extend along the short side of the oxygen delivering mask 1, and the other part of the tube 16b can each have any length.

The part of the tube 16b, which part extends along the short side of the oxygen delivering mask 1, is adhered to at least one of sheets between adjacent ones of which a space in which oxygen is stored is formed. Note that the other part of the tube 16b can be adhered to, but not limited to, at least one of the sheets, as with the case of the part of the tube 16b, which part extends along the short side of the oxygen delivering mask 1. In a case of this configuration, a connecting part 9a is an adhesive member which causes the tube 16b to be adhered to at least one of the sheets.

For example, in a case of Embodiment 2, the tube 16b is adhered to at least one of the first sheet 2 and the second sheet 3, between which the gas storing part 4 is formed, so as to be located between the first sheet 2 and the second sheet 3 (see FIG. 3). In a case of Embodiment 3, the tube 16b is adhered to at least one of the second sheet 3 and the third sheet 7, between which the gas storing part 4 is formed, so as to be located between the second sheet 3 and the third sheet 7 (see FIG. 4). In a case of Embodiment 6, the tube 16b is adhered to the first sheet 2a (see FIG. 8). In a case of Embodiment 7, the tube 16b is adhered to the outer side of the first sheet 2b, that is, to the outer side of the oxygen delivering mask 1g.

As illustrated in (b) of FIG. 11, in a case where a gas is supplied via the gas supply port(s) 6 of the tube 16b, a space is formed, at a central portion of the oxygen delivering mask 1, between the adjacent ones of the sheets, and then expanded. Therefore, it is possible to store the gas, in a larger amount, in the space formed between the adjacent ones of the sheets.

(c) of FIG. 11 is a view illustrating a configuration in which a member 9b, via which a gas supply port located at an end of the gas tube 16 illustrated in FIG. 1 is connected to an oxygen delivering mask 1, is adhered to the oxygen delivering mask 1. In a case of the configuration illustrated in (c) of FIG. 11, the member 9b is a connecting part. For example, in a case of Embodiment 2, the member 9b is adhered to at least one of the first sheet 2 and the second sheet 3 so as to be located between the first sheet 2 and the second sheet 3. According to the above configuration, inserting the gas supply port of the gas tube 16 to the member 9b causes oxygen to be delivered to the oxygen delivering mask 1. Therefore, it is possible to use the oxygen delivering mask 1 as a disposable mask. Accordingly, a user is capable of always using a clean oxygen delivering mask 1.

(d) of FIG. 11 is a view illustrating a configuration in which a gas supply pathway is formed so as to extend along a short side of an oxygen delivering mask 1. The gas supply pathway illustrated in (d) of FIG. 11 is a flow passage 50 which is formed by adhering adjacent ones of a plurality of sheets between adjacent ones of which a space in which oxygen is stored is formed. There are two ways of using the flow passage 50. As a first way, the flow passage 50 is used in such a way that the gas tube 16 illustrated in FIG. 1 is inserted in the flow passage 50. Note that a gas supply port is formed in any portion of each of the gas tube 16 and the flow passage 50. In a case of the first way, a connecting part 9c is the flow passage 50 itself.

As a second way, the flow passage 50 is used in such a way that the gas tube 16 illustrated in FIG. 1 is inserted in an inlet port 51 of the flow passage 50 so that oxygen passes through the flow passage 50. In a case of the second way, the connecting part 9c is the inlet port 51. Note that the flow passage 50 has a hole through which oxygen is supplied to the oxygen delivering mask 1. Note also that the flow passage 50 is not limited to an example illustrated in (d) of FIG. 11 in terms of a length and a shape. For example, the flow passage 50 can have a length shorter than that of the short side of the oxygen delivering mask 1, and can have an L shape as illustrated in (b) of FIG. 11.

According to the configuration, the gas supply pathway and the connecting part 9c are formed by adhering the adjacent ones of the plurality of sheets, between adjacent ones of which the space in which oxygen is stored is formed. This allows a user to freely use the oxygen delivering mask 1 as a disposable mask. Accordingly, the user is capable of always using a clean oxygen delivering mask 1.

As illustrated in (a) and (b) of FIG. 11, the tube 16a and the tube 16b, each of which is adhered to the oxygen delivering mask 1, can be each connected to and adhered to a corner of the oxygen delivering mask 1. Further, as illustrated in (c) and (d) of FIG. 11, the connecting part can be arranged such that the gas supply port of the gas tube, serving as a gas supply pathway, is connected to a corner of the oxygen delivering mask 1.

According to the above configurations, in a case where a user uses the oxygen delivering mask 1, the user is capable of placing the gas supply pathway, together with the attaching part 15 illustrated in FIG. 1, on an ear of the user. This allows a reduction in feeling of strangeness in appearance, and allows the user to wear the oxygen delivering mask 1 without worrying about the public eye, as with the case of a conventional surgical mask.

Further, the connecting part 9, the connecting part 9a, the member (connecting part) 9b, and the connecting part 9c, each illustrated in FIG. 11, can be each arranged such that the gas supply port(s) 6 of the gas supply pathway is/are connected to at least one of adjacent ones (for example, the first sheet and the second sheet) of the plurality of sheets so as to be located between the adjacent ones (for example, between the first sheet and the second sheet) of the plurality of sheets. According to such a configuration, since the gas supply port(s) 6 is/are located between the adjacent ones (between the first sheet and the second sheet) of the plurality of sheets, it is possible to absolutely store, between the adjacent ones of the plurality of sheets, oxygen supplied via the gas supply port(s) 6. This absolutely causes oxygen supplied from outside the oxygen delivering mask 1 to permeate the plurality of sheets and be supplied to a user. It is therefore possible to maintain more suitable humidity between the oxygen delivering mask 1 and the face of the user, and possible to more effectively provide, to the user, a gas therapy with use of the oxygen delivering mask 1.

[Example of how Oxygen Delivering Mask is Used]

Use of an oxygen delivering mask in accordance with each of Embodiments 1 through 8 will be described below with reference to (a) and (b) of FIG. 12. Note that the following description will take the oxygen delivering mask 1c in accordance with Embodiment 4 as an example. As illustrated in (a) of FIG. 12, a mask body of the oxygen delivering mask 1c is made up of the first sheet 2 and the second sheet 3a which are each a flexible sheet and which are layered on each other. The oxygen delivering mask 1c has, for example, a rectangular shape. The oxygen delivering mask 1c includes attaching parts 15 provided on respective short sides of the oxygen delivering mask 1c which short sides face each other.

Figure 12:
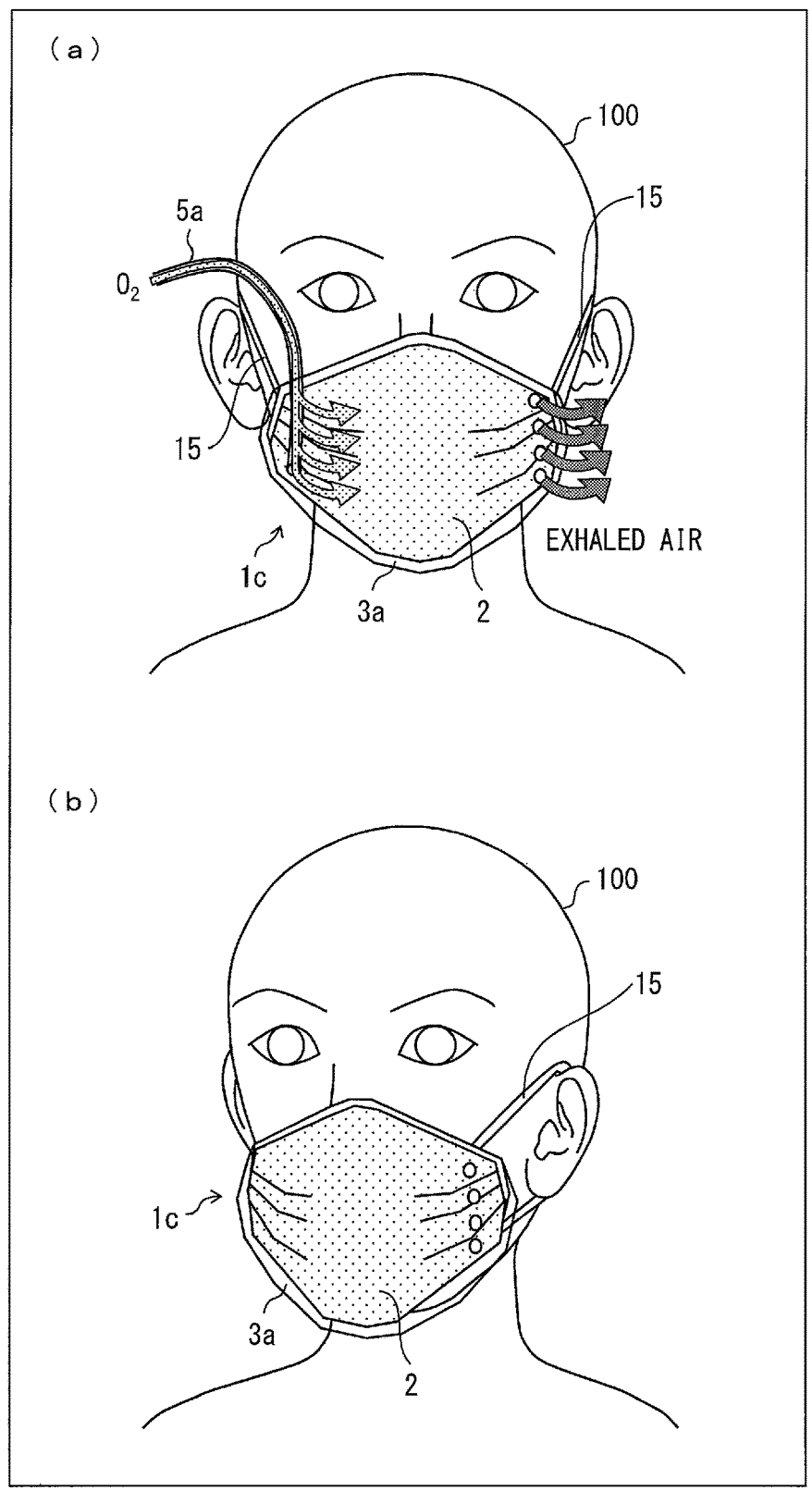
FIG. 12 is a view illustrating an example of how the oxygen delivering mask in accordance with Embodiment 4 is used.

According to the oxygen delivering mask 1c illustrated in (a) of FIG. 12, the gas supply pathway 5a is, as has been described, provided between the first sheet 2 and the second sheet 3a so as to extend along one of the short sides of the oxygen delivering mask 1c, and oxygen is supplied to a space formed between the first sheet 2 and the second sheet 3a. Air exhaled by a user 100 passes through the holes formed so as to be arranged along the other one of the short sides of the oxygen delivering mask 1c which other one faces the ones of the shorts sides along which one the gas supply pathway 5a is provided so as to extend, and is then discharged outside the oxygen delivering mask 1c.

In a case where the oxygen delivering mask 1c is used, the oxygen delivering mask 1c is worn by the user 100 in such a way that (i) the attaching parts 15 are placed on the respective both ears of the user 100 and (ii) the first sheet 2 and the second sheet 3a cover the nose and the mouth of the user 100 (see (b) of FIG. 12). Note that, in a case where each of the first sheet 2 and the second sheet 3a is pleated, pleats of each of the first sheet 2 and the second sheet 3a are suitably spread so that the oxygen delivering mask 1c has such a three-dimensional shape that the nose and the mouth of the user 100 are covered.

(Comparison with Conventional Technique)

(a) of FIG. 13 is a view illustrating an example of how a nasal cannula 101 of a conventional technique is used. The nasal cannula 101, which is made of a tube, is used in such a way that (i) the nasal cannula 101 is placed on the both ears of a user 100 as illustrated in (a) of FIG. 13 and (ii) supply ports, via each of which oxygen is supplied, are inserted in the nasal cavity of the user 100. Therefore, according to the nasal cannula 101, the nostrils of the user 100 may be dried due to a flow of supplied oxygen. This may also cause a problem that use of the nasal cannula 101 leads to infection or disorder of swallowing function due to dryness.

In contrast, the oxygen delivering mask 1c illustrated in (a) of FIG. 12 is configured such that oxygen supplied through the gas supply pathway 5 is stored in a space formed between adjacent ones of the plurality of sheets (for example, a space formed between the first sheet 2 and the second sheet 3a). That is, according to the oxygen delivering mask 1c, oxygen is not directly supplied to the nose and the mouth of the user 100. Therefore, the nostrils and the mouth of the user 100 are not dried due to a flow of supplied oxygen. The oxygen delivering mask 1 thus causes suitable humidity to be maintained between the oxygen delivering mask 1 and the face of the user, thereby not giving a feeling of discomfort to the user which feeling of discomfort is caused by dryness of the mouth during use of a mask.

(b) of FIG. 13 is a view illustrating an example of how a respiratory mask 102 of a conventional technique is used. The respiratory mask 102 has such a shape that the nose and the mouth of a user are covered, and is made of plastic. A peripheral portion of the respiratory mask 102 is in absolute contact with the face of a user 100, and oxygen is supplied to a closed space formed between the face of the user 100 and the respiratory mask 102. In contrast, the oxygen delivering mask 1c illustrated in (a) of FIG. 12 is a flexible mask, and a peripheral portion of the mask body (the first sheet 2 and the second sheet 3a) is not in absolute contact with the face of the user 100. Therefore, the oxygen delivering mask 1c illustrated in (a) of FIG. 12 does not give a feeling of discomfort to the user 100 which feeling of discomfort is caused by pressure of a mask against the face of the user 100, as compared with the respiratory mask 102 illustrated in (b) of FIG. 13.

For the above reasons, the oxygen delivering mask 1c illustrated in (a) of FIG. 12 is not removed by the user 100 himself/herself due to a feeling of discomfort while the user 100 is wearing the oxygen delivering mask 1c. In particular, in a case where the user 100 is in delirium or is not in good cognitive status, the oxygen delivering mask 1c is effective, and allows an oxygen therapy, in which oxygen is supplied to the user 100, to be smoothly provided to the user 100.

Furthermore, in a case where the mask body of the oxygen delivering mask 1c illustrated in (a) of FIG. 12 is made up of sheets which constitute a mask body of a mass-produced surgical mask, it is possible to reduce a cost of the oxygen delivering mask 1c, as compared with the nasal cannula 101 illustrated in (a) of FIG. 13 and the respiratory mask 102 illustrated in (b) of FIG. 13. Therefore, it is possible to use the oxygen delivering mask 1c as a disposable mask.

Moreover, as illustrated in (b) of FIG. 12, an appearance of the user 100 wearing the oxygen delivering mask 1c is substantially equal to that of the user 100 wearing a widespread surgical mask. Therefore, the user is capable of wearing the oxygen delivering mask 1c without worrying about the public eye, as with the case of a conventional surgical mask. In particular, in a case where an oxygen therapy needs to be provided to the user in a facility located outside a hospital (for example, in a case where an oxygen therapy needs to be provided to the user at home), an oxygen therapy in which the oxygen delivering mask 1c is used is easily accepted by the user.

[Evaluation Results]

(Outline of Test)

FIG. 14 is a view illustrating an outline of a test. As illustrated in FIG. 14, an oxygen delivering mask 1, which is a mask to be evaluated, is worn by a user 100, and a gas supply port of a gas supply pathway 5, which is an oxygen supply tube, is set in a vicinity of the mouth (right end of the mouth) of the user 100. An end of a measurement probe 103 is set on a lower left side of the mouth of the user 100 in a state where the end of the measurement probe 103 is fixed to the lower left side of the mouth of the user 100.

In the test, a concentration (%) of oxygen and a partial pressure (mmHg) of carbon dioxide, which oxygen and carbon dioxide are each contained in air exhaled by the user 100 wearing the oxygen delivering mask 1, are measured. Similarly, a concentration (%) of oxygen and a partial pressure (mmHg) of carbon dioxide, which oxygen and carbon dioxide are each contained in air inhaled by the user 100 wearing the oxygen delivering mask 1, are measured. Note that the test is carried out while the user 100 is breathing through the mouth, and a breathing rate is set to a normal rate (normal breathing, 3.5 seconds per breath) and a fast rate (fast breathing, 1.5 seconds per breath).

(Evaluation Objects)

FIG. 15 is a view schematically illustrating a configuration of each of evaluation objects. Masks used as the evaluation objects are a conventional surgical mask, a sample A, a sample B in accordance with Embodiment 2, a sample C in accordance with Embodiment 1, and a conventional respiratory mask (see (b) of FIG. 13). Note that the conventional surgical mask, the sample A, and the conventional respiratory mask are evaluation objects which are compared with each of the sample B and the sample C.

The conventional surgical mask, which is one of the evaluation objects, is made up of three non-woven fabrics.

Note that oxygen is not supplied to the conventional surgical mask. The conventional respiratory mask, which is one of the evaluation objects, is made of plastic. The respiratory mask 102 illustrated in (b) of FIG. 13 serves as the conventional respiratory mask.

The sample A, which is one of the evaluation objects, is made up of non-woven fabrics "a" through "c" which are identical to each other in gas permeability. The sample A is configured such that oxygen is supplied between (i) a sheet which is made up of the non-woven fabric "a" and the non-woven fabric "b" and which is located on a side of the mouth of the user wearing the sample A and (ii) the non-woven fabric "c" which is located on an outside air side. Therefore, oxygen supplied to the sample A permeates the sheet made up of the non-woven fabric "a" and the non-woven fabric "b," and is supplied to the user wearing the sample A.

Note that the sheet made up of the non-woven fabric "a" and the non-woven fabric "b" has gas permeability lower than that of the non-woven fabric "c." The oxygen supplied to the sample A can be emitted in any direction, provided that the any direction is different from such a direction that the oxygen is emitted toward the sheet made up of the non-woven fabric "a" and the non-woven fabric "b."

The sample B, which is one of the evaluation objects, is made up of a non-woven fabric "a," a non-woven fabric "b," and a non-woven fabric "c." The sample B is configured such that oxygen is supplied between (i) the non-woven fabric "a" (first sheet) which is located on a side of the mouth of the user wearing the sample B and (ii) a sheet (second sheet) which is made up of the non-woven fabric "b" and the non-woven fabric "c" and which is located on an outside air side. Therefore, oxygen supplied to the sample B permeates the non-woven fabric "a," and is supplied to the user wearing the sample B. Note that the non-woven fabric "a" has gas permeability higher than that of the sheet made up of the non-woven fabric "b" and the non-woven fabric "c."

The sample C, which is one of the evaluation objects, is made up of a non-woven fabric "a," a non-woven fabric "b," a non-woven fabric "c," and a film sheet. The sample C is configured such that oxygen is supplied between (i) a sheet (first sheet) which is made up of the non-woven fabric "a," the non-woven fabric "b," and the non-woven fabric "c" and which is located on a side of the mouth of the user wearing the sample C and (ii) the film sheet (second sheet) which is located on an outside air side. Therefore, oxygen supplied to the sample C permeates the sheet made up of the non-woven fabric "a," the non-woven fabric "b," and the non-woven fabric "c," and is supplied to the user wearing the sample C. Note that the sheet made up of the non-woven fabric "a," the non-woven fabric "b," and the non-woven fabric "c" has gas permeability higher than that of the film sheet.

(Measurement Results)

FIG. 16 is a graph showing results of measurement carried out with respect to the evaluation objects illustrated in FIG. 15. Note that the oxygen delivering mask 1 is worn by a patient whose respiratory organ does not function normally. For this reason, each of the sample B and the sample C in accordance with the embodiments of the present invention is compared with the evaluation objects other than the sample B and the sample C for evaluation.

(Results of Measurement During Normal Breathing)

An upper left graph in FIG. 16 shows results of measuring oxygen concentrations during normal breathing. As is clear from the upper left graph, a concentration of oxygen contained in air inhaled by the user wearing the sample B and a concentration of oxygen contained in air exhaled by the user wearing the sample B are each not less than 25%. A concentration of oxygen contained in air inhaled by the user wearing the sample C is approximately 25%, and a concentration of oxygen contained in air exhaled by the user wearing the sample C is not less than 30%.

On the other hand, a concentration of oxygen contained in air inhaled by the user wearing the conventional respiratory mask is approximately 30%, and a concentration of oxygen contained in air exhaled by the user wearing the conventional respiratory mask is approximately 25%. Therefore, it is evaluated that, during normal breathing, a concentration of oxygen contained in each of inhaled air and exhaled air in a case where the sample B in accordance with an embodiment of the present invention is in use is equal to that of oxygen contained in a corresponding one of inhaled air and exhaled air in a case where the conventional respiratory mask is in use. The same applies to a case where the sample C in accordance with an embodiment of the present invention is in use.

A concentration of oxygen contained in air inhaled by the user wearing no mask and a concentration of oxygen contained in air exhaled by the user wearing no mask are each approximately 20%. A concentration of oxygen contained in air inhaled by the user wearing the conventional surgical mask and a concentration of oxygen contained in air exhaled by the user wearing the conventional surgical mask are each not more than 20%. Therefore, it is evaluated that a concentration of oxygen contained in each of inhaled air and exhaled air in a case where the sample B in accordance with an embodiment of the present invention is in use is higher than that of oxygen contained in a corresponding one of inhaled air and exhaled air in a case where no mask is in use, and is higher than that of oxygen contained in a corresponding one of inhaled air and exhaled air in a case where the conventional surgical mask is in use. The same applies to a case where the sample C in accordance with an embodiment of the present invention is in use. That is, it can be said that each of the sample B and the sample C is effective as a mask for delivering oxygen to a user.

A concentration of oxygen contained in air inhaled by the user wearing the sample A and a concentration of oxygen contained in air exhaled by the user wearing the sample A are each approximately 20%. Therefore, it is evaluated that a concentration of oxygen contained in each of inhaled air and exhaled air in a case where the sample A is in use is lower than that of oxygen contained in a corresponding one of inhaled air and exhaled air in a case where the conventional respiratory mask is in use. That is, it can be said that, during normal breathing, the sample A is low in function of supplying oxygen to a user wearing a mask, as compared with the sample B and the sample C. Accordingly, it can be said that the configuration of each of the sample B and the sample C is more excellent than that of the sample A in terms of supplying oxygen to a user during normal breathing.

An upper right graph in FIG. 16 shows results of measuring carbon dioxide partial pressures during normal breathing. As is clear from the upper right graph, a partial pressure of carbon dioxide contained in air inhaled by the user wearing the sample B is approximately 0 (zero) mmHg because air exhaled by the user is more easily diluted by ambient air. A partial pressure of carbon dioxide contained in air exhaled by the user wearing the sample B is approximately 30 mmHg. A partial pressure of carbon dioxide contained in air inhaled by the user wearing the sample C is approximately 0 (zero) mmHg because air exhaled by the user is more easily diluted by ambient air. A partial pressure of carbon dioxide contained in air exhaled by the user wearing the sample C is less than 30 mmHg.

On the other hand, a partial pressure of carbon dioxide contained in air inhaled by the user wearing the conventional respiratory mask is 0 (zero) mmHg, and a partial pressure of carbon dioxide contained in air exhaled by the user wearing the conventional respiratory mask is approximately 30 mmHg. Therefore, it is evaluated that, during normal breathing, a concentration of carbon dioxide contained in each of inhaled air and exhaled air in a case where the sample B in accordance with an embodiment of the present invention is in use is equal to that of carbon dioxide contained in a corresponding one of inhaled air and exhaled air in a case where the conventional respiratory mask is in use. The same applies to a case where the sample C in accordance with an embodiment of the present invention is in use.

A partial pressure of carbon dioxide contained in air inhaled by the user wearing the conventional surgical mask is approximately 0 (zero) mmHg, and a partial pressure of carbon dioxide contained in air exhaled by the user wearing the conventional surgical mask is less than 30 mmHg. Therefore, it is evaluated that, during normal breathing, a concentration of carbon dioxide contained in each of inhaled air and exhaled air in a case where the sample B in accordance with an embodiment of the present invention is in use is equal to that of carbon dioxide contained in a corresponding one of inhaled air and exhaled air in a case where the conventional surgical mask is in use. The same applies to a case where the sample C in accordance with an embodiment of the present invention is in use. Note that a partial pressure of carbon dioxide contained in air inhaled by the user wearing no mask is 0 (zero) mmHg, and a partial pressure of carbon dioxide contained in air exhaled by the user wearing no mask is not less than 5 mmHg.

A partial pressure of carbon dioxide contained in air inhaled by the user wearing the sample A is several millimeters of mercury, and a partial pressure of carbon dioxide contained in air exhaled by the user wearing the sample A is approximately 35 mmHg. Therefore, it is evaluated that a concentration of carbon dioxide contained in each of inhaled air and exhaled air in a case where the sample A is in use is higher than that of carbon dioxide contained in a corresponding one of inhaled air and exhaled air in a case where the conventional respiratory mask is in use. That is, it can be said that, during normal breathing, the sample A is low in function of discharging, outside a mask, air (carbon dioxide) exhaled by a user wearing the mask, as compared with the sample B and the sample C. Accordingly, it can be said that the configuration of each of the sample B and the sample C is more excellent than that of the sample A in terms of discharging, outside a mask, air (carbon dioxide) exhaled by a user during normal breathing.

(Results of Measurement During Fast Breathing)

A lower left graph in FIG. 16 shows results of measuring oxygen concentrations during fast breathing. As is clear from the lower left graph, a concentration of oxygen contained in air inhaled by the user wearing the sample B is approximately 25%, and a concentration of oxygen contained in air exhaled by the user wearing the sample B is not less than 30%. A concentration of oxygen contained in air inhaled by the user wearing the sample C is not less than 25%, and a concentration of oxygen contained in air exhaled by the user wearing the sample C is not less than 30%.

On the other hand, a concentration of oxygen contained in air inhaled by the user wearing the conventional respiratory mask is not less than 25%, and a concentration of oxygen contained in air exhaled by the user wearing the conventional respiratory mask is approximately 25%. Therefore, it is evaluated that, during fast breathing, a concentration of oxygen contained in each of inhaled air and exhaled air in a case where the sample B in accordance with an embodiment of the present invention is in use is equal to that of oxygen contained in a corresponding one of inhaled air and exhaled air in a case where the conventional respiratory mask is in use. The same applies to a case where the sample C in accordance with an embodiment of the present invention is in use.

A concentration of oxygen contained in air inhaled by the user wearing the conventional surgical mask and a concentration of oxygen contained in air exhaled by the user wearing the conventional surgical mask are each not more than 20%. Therefore, it is evaluated that a concentration of oxygen contained in each of inhaled air and exhaled air in a case where the sample B in accordance with an embodiment of the present invention is in use is higher than that of oxygen contained in a corresponding one of inhaled air and exhaled air in a case where the conventional surgical mask is in use. The same applies to a case where the sample C in accordance with an embodiment of the present invention is in use. That is, it can be said that each of the sample B and the sample C is effective as a mask for delivering oxygen to a user.

A concentration of oxygen contained in air inhaled by the user wearing the sample A and a concentration of oxygen contained in air exhaled by the user wearing the sample A are each approximately 20%. Therefore, it is evaluated that a concentration of oxygen contained in each of inhaled air and exhaled air in a case where the sample A is in use is lower than that of oxygen contained in a corresponding one of inhaled air and exhaled air in a case where the conventional respiratory mask is in use. That is, it can be said that, during fast breathing, the sample A is low in function of supplying oxygen to a user wearing a mask, as compared with the sample B and the sample C. Accordingly, it can be said that the configuration of each of the sample B and the sample C is more excellent than that of the sample A in terms of supplying oxygen to a user during fast breathing.

A lower right graph in FIG. 16 shows results of measuring carbon dioxide partial pressures during fast breathing. As is clear from the lower right graph, a partial pressure of carbon dioxide contained in air inhaled by the user wearing the sample B is approximately 0 (zero) mmHg because air exhaled by the user is more easily diluted by ambient air. A partial pressure of carbon dioxide contained in air exhaled by the user wearing the sample B is approximately 25 mmHg. A partial pressure of carbon dioxide contained in air inhaled by the user wearing the sample C is approximately 0 (zero) mmHg because air exhaled by the user is more easily diluted by ambient air. A partial pressure of carbon dioxide contained in air exhaled by the user wearing the sample C is not less than 25 mmHg.

On the other hand, a partial pressure of carbon dioxide contained in air inhaled by the user wearing the conventional respiratory mask is approximately 0 (zero) mmHg, and a partial pressure of carbon dioxide contained in air exhaled by the user wearing the conventional respiratory mask is approximately 20 mmHg. A partial pressure of carbon dioxide contained in air inhaled by the user wearing the conventional surgical mask is approximately 0 (zero) mmHg, and a partial pressure of carbon dioxide contained in air exhaled by the user wearing the conventional surgical mask is approximately 25 mmHg. Therefore, it is evaluated that, during fast breathing, a concentration of carbon dioxide contained in each of inhaled air and exhaled air in a case where the sample B in accordance with an embodiment of the present invention is in use is higher than that of carbon dioxide contained in a corresponding one of inhaled air and exhaled air in a case where the conventional respiratory mask is in use. The same applies to a case where the sample C in accordance with an embodiment of the present invention is in use. Meanwhile, it is evaluated that, during fast breathing, a concentration of carbon dioxide contained in each of inhaled air and exhaled air in a case where the sample B in accordance with an embodiment of the present invention is in use is equal to that of carbon dioxide contained in a corresponding one of inhaled air and exhaled air in a case where the conventional surgical mask is in use. The same applies to a case where the sample C in accordance with an embodiment of the present invention is in use.

A partial pressure of carbon dioxide contained in air inhaled by the user wearing the sample A is less than 5 mmHg, and a partial pressure of carbon dioxide contained in air exhaled by the user wearing the sample A is approximately 30 mmHg. Therefore, it is evaluated that a concentration of carbon dioxide contained in each of inhaled and exhaled air in a case where the sample A is in use is higher than that of carbon dioxide contained in a corresponding one of inhaled air and exhaled air in a case where the sample B is in use, and is higher than that of carbon dioxide contained in a corresponding one of inhaled air and exhaled air in a case where the sample C is in use. That is, it can be said that, during fast breathing, the sample A is low in function of discharging, outside a mask, air (carbon dioxide) exhaled by a user wearing the mask, as compared with the sample B and the sample C. Accordingly, it can be said that the configuration of each of the sample B and the sample C is more excellent than that of the sample A in terms of discharging, outside a mask, air (carbon dioxide) exhaled by a user.

Embodiment 9

(a) of FIG. 17 is a view illustrating an example of how an oxygen delivering mask 1i in accordance with Embodiment 9 is worn. The oxygen delivering mask (gas storing mask) 1i in accordance with Embodiment 9 is different from the foregoing oxygen delivering masks in that a second sheet 3i overlaps a first sheet 2, that is, the second sheet 3i extends over part of the first sheet 2. Note that the "part of the first sheet 2" indicates, for example, an upper part of the first sheet 2 in a state where the oxygen delivering mask 1i is worn by a user 100 (see (a) of FIG. 17). The oxygen delivering mask 1i is configured such that the second sheet 3i extends over the part of the first sheet 2 which part covers the nose of the user 100. In a case of such a configuration, the second sheet 3i does not extend over a lower part of the first sheet 2 in the state where the oxygen delivering mask 1i is worn by the user 100. Note that, as with the case of the foregoing oxygen delivering masks, the oxygen delivering mask 1i is also configured such that a gas storing part 4 is formed between the first sheet 2 and the second sheet 3i by oxygen passing through a gas supply pathway 5 and being stored between the first sheet 2 and the second sheet 3i.

According to the above configuration, the second sheet 3i, which has gas permeability lower than that of the first sheet 2, extends over the part of the first sheet 2. This allows air exhaled by the user 100 to (i) permeate the other part of the first sheet 2 over which other part the second sheet 3i does not extend and (ii) be discharged outside the oxygen delivering mask 1i, in a case where the user 100 exhales. Therefore, it is possible to reduce an amount of air which is exhaled by the user 100 and which permeates the part of the first sheet 2, over which part the second sheet 3*i* extends, and is mixed with a gas stored in the gas storing part 4.

Further, in a case where supply of oxygen to the gas storing part 4 through the gas supply pathway 5 is stopped for any reason, outside air easily (i) permeates the other part of the first sheet 2 over which other part the second sheet 3*i* does not extend and (ii) is supplied to the body of the user 100 from outside the oxygen delivering mask 1*i*, when the user 100 inhales.

Note that the part of the first sheet 2 over which part the second sheet 3*i* extends can be part which covers the nose of the user 100 or can be alternatively part which covers the mouth and the nose of the user 100. Even in a former case, when the user breathes through the mouth, the gas stored in the gas storing part 4 is capable of permeating the first sheet 2 and being supplied to the body of the user.

(b) of FIG. 17 is a view illustrating a configuration of an oxygen delivering mask 1*j* which is a variation of Embodiment 9. The oxygen delivering mask (gas storing mask) 1*j* is different from the oxygen delivering mask 1*i* illustrated in (a) of FIG. 17 in that the oxygen delivering mask 1*j* includes a third sheet 7*j* provided between a first sheet 2 and a second sheet 3*i*. The third sheet 7*j* has gas permeability lower than that of the first sheet 2, and is provided on part of the first sheet 2 over which part the second sheet 3*i* extends. Oxygen which passes through a gas supply pathway 5 is supplied between the second sheet 3*i* and the third sheet 7*j*, as with the case of the oxygen delivering mask 1*b* illustrated in FIG. 4. The third sheet 7*j* has a plurality of holes 72 through which oxygen stored in a gas storing part 4 is supplied to the body of a user.

Each of the plurality of holes 72 formed in the third sheet 7*j* has a size which causes oxygen stored in the gas storing part 4 to be supplied to the body of the user. The number of the plurality of holes 72 can be any number. For example, each of the plurality of holes 72 has a size similar to that of a human finger, and the plurality of holes 72 are formed at respective positions which are close to the mouth and the nostrils (a region under the nose) of the user in a case where the user wears the oxygen delivering mask 1*j*. Forming the plurality of holes 72 at such respective positions allows oxygen stored in the gas storing part 4 to pass through the plurality of holes 72 and be smoothly supplied to the body of the user, in both of a case where the user breathes through the mouth and a case where the user breathes through the nose.

According to the above configuration, the gas storing part 4 is formed between the second sheet 3*i* and the third sheet 7*j* each of which has gas permeability lower than that of the first sheet 2. Therefore, air exhaled by the user is prevented from permeating the first sheet 2 and the third sheet 7*j* and being mixed with a gas stored in the gas storing part 4. Furthermore, the third sheet 7*j* has the plurality of holes 72. This allows the gas stored in the gas storing part 4 to have some degree of directionality when supplied to the body of the user, in a case where the user inhales. That is, in a case where the user inhales, the gas stored in the gas storing part 4 passes through the plurality of holes 72, and the gas which has passed through the plurality of holes 72 moves toward and is accurately supplied to the body (the mouth or the nose) of the user.

Embodiment 10

(a) of FIG. 18 is a view illustrating an example of how an oxygen delivering mask 1*k* in accordance with Embodiment 10 is worn. The oxygen delivering mask (gas storing mask) 1*k* in accordance with Embodiment 10 is different from the oxygen delivering mask 1*a* illustrated in FIG. 3 in that the oxygen delivering mask 1*k* includes (i) a first sheet 2*k* having a hole 73 and (ii) a second sheet 3*k* having a hole 81. Note that, as with the case of the oxygen delivering mask 1*a* illustrated in FIG. 3, the oxygen delivering mask 1*k* is also configured such that a gas storing part 4 is formed between the first sheet 2*k* and the second sheet 3*k* by oxygen passing through a gas supply pathway 5 and being stored between the first sheet 2*k* and the second sheet 3*k*.

The hole 73 formed in the first sheet 2*k* is a hole through which oxygen stored in the gas storing part 4 is supplied to the body of a user. For example, the hole 73 has a size similar to that of the mouth of the user wearing the oxygen delivering mask 1*k*. The hole 73 is formed at a position which is in a vicinity of the mouth of the user in a case where the user wears the oxygen delivering mask 1*k*. The hole 81 formed in the second sheet 3*k* is a hole through which air exhaled by the user is discharged. For example, the hole 81 has a size identical to that of the hole 73 formed in the first sheet 2*k*. The hole 81 is formed at such a position that air which has been exhaled by the user and passed through the hole 73 smoothly passes through the hole 81. Note that the first sheet 2*k* and the second sheet 3*k* can have a single hole 73 and a single hole 81, respectively, each of which has a size similar to that of the mouth of the user as described above. Alternatively, the first sheet 2*k* can have a plurality of micropores formed in a range which is similar in size to the mouth of the user, and the second sheet 3*k* can have a plurality of micropores formed in a range which is similar in size to the mouth of the user.

(b) of FIG. 18 is a view illustrating a configuration of the oxygen delivering mask 1*k*. The hole 73, formed in the first sheet 2*k*, and the hole 81, formed in the second sheet 3*k*, constitute a pathway through which air exhaled by the user is discharged outside the oxygen delivering mask 1*k*. Therefore, due to force of user's exhalation, the air exhaled by the user passes through the hole 73 and the hole 81, and is then discharged outside the oxygen delivering mask 1*k*. It is therefore possible to absolutely prevent the air exhaled by the user from being mixed with a gas stored in the gas storing part 4. Furthermore, since oxygen continues to be supplied to the gas storing part 4, the oxygen stored in the gas storing part 4 passes through the hole 73 and is supplied to the body of the user, in a case where the user inhales.

Note that the above-described oxygen delivering mask has an appearance similar to that of a conventionally-widespread mask. For example, the oxygen delivering mask can be a mask made up of sheets each of which is pleated as illustrated in FIG. 1 and so on. Alternatively, the oxygen delivering mask can be a mask that is made up of sheets each of which is folded in two and that is used, as a three-dimensional mask, in a state where such two-folded sheets are spread. Alternatively, the oxygen delivering mask can be a mask that is made up of thick non-woven fabrics and that has such a domical shape that the nose and the mouth of the user are covered.

[Supplementary Note]

The present invention is not limited to the embodiments, but can be altered by a skilled person in the art within the scope of the claims. An embodiment derived from a proper combination of technical means each disclosed in a different embodiment is also encompassed in the technical scope of the present invention.

Note that the present invention can be expressed as below. That is, an oxygen delivering mask in accordance with an aspect of the present invention is an oxygen delivering mask including: a mask body which includes (i) a fiber sheet made up of a plurality of fiber sheets which are layered on each other and (ii) a film sheet covering an upper surface of the fiber sheet, the fiber sheet and the film sheet being jointed together at their respective peripheral portions; an attaching part 15 which causes the mask body to be attached to the body of a user; and a gas tube through which an oxygen gas is delivered to a gas storing part formed between the fiber sheet and the film sheet, the gas storing part being formed in such a way that a space is formed and expanded by delivered oxygen gas.

The oxygen delivering mask in accordance with an aspect of the present invention can be arranged such that the film sheet is pleated. Furthermore, the oxygen delivering mask in accordance with an aspect of the present invention can be arranged such that each of the fiber sheet and the film sheet is pleated so that the film sheet has pleats each of which has a width greater than that of each of pleats of the fiber sheet and/or the number of which is greater than that of the pleats of the fiber sheet.

Furthermore, the oxygen delivering mask in accordance with an aspect of the present invention can be arranged such that the film sheet is made of any one of a polyethylene resin, a polyvinylchloride resin, a polyamide resin, and a polyethylene terephthalate resin.

Moreover, the oxygen delivering mask in accordance with an aspect of the present invention can be arranged such that the gas tube (a) has (i) a tube part joined to a corner of the mask body and (ii) an end opened to a central portion of the mask body, (b) extends from the mask body, and (c) has a connector via which the gas tube is connected to an oxygen supply tube.

The oxygen delivering mask in accordance with an aspect of the present invention thus includes (i) the fiber sheet that is made of a fiber of which, for example, a woven fabric, a non-woven fabric, or non-woven paper is made and that is flexible and light-weight and (ii) the film sheet that is flexible and light-weight. Therefore, the oxygen delivering mask less gives a feeling of discomfort to a user wearing the oxygen delivering mask. This allows the user to wear the oxygen delivering mask for long hours and to wear the oxygen delivering mask with a feeling similar to that the user receives from use of a surgical mask. Furthermore, the oxygen delivering mask in accordance with an aspect of the present invention is configured such that the gas storing part serves as a gas reservoir. Therefore, it is possible to easily and effectively supply oxygen to a patient.

SUMMARY

In order to attain the above object, a gas storing mask in accordance with an aspect of the present invention is a gas storing mask in which a gas is stored, the gas storing mask including: a plurality of sheets, the gas, which is supplied from outside the gas storing mask, being stored in a space formed between adjacent ones of the plurality of sheets. According to the above configuration, a gas supplied from outside the gas storing mask is stored in the space formed between the adjacent ones of the plurality of sheets. This causes the gas stored in the space to, in connection with breathing of a user, permeate the plurality of sheets and be supplied to the user. Therefore, the gas storing mask causes suitable humidity to be maintained between the gas storing mask and the face of the user, thereby not giving a feeling of discomfort to the user which feeling of discomfort is caused by dryness of the mouth during use of a mask. Accordingly, the user is capable of comfortably wearing the gas storing mask for long hours and receiving, for long hours, a gas therapy (for example, oxygen therapy) in which the gas storing mask is used.

Further, the gas storing mask in accordance with an aspect of the present invention can be arranged such that at least two of the plurality of sheets are different from each other in gas permeability. According to the above configuration, the gas stored in the space formed between the adjacent ones of the plurality of sheets (i) easily permeates one of the at least two of the plurality of sheets which one has higher gas permeability and (ii) is easily discharged outside the space. Further, the gas stored in the space (i) does not easily permeate the other one of the at least two of the plurality of sheets which other one has lower gas permeability and (ii) does not easily leak out of the gas storing mask. Therefore, in a case where the gas storing mask is worn by the user such that the one of the at least two of the plurality of sheets, which one has higher gas permeability, is located on a user's mouth side, it is possible to efficiently provide, to the user, a gas therapy in which the gas storing mask is used.

Furthermore, according to the above configuration, in a case where the gas continues to be supplied to the space formed between the adjacent ones of the plurality of sheets, a pressure of the gas stored in the space is increased. This causes the gas stored in the space to intend to permeate the one of the at least two of the plurality of sheets, which one has higher gas permeability, and leak out of the space. Meanwhile, in a case where the gas storing mask is worn by the user such that the one of the at least two of the plurality of sheets, which one has higher gas permeability, is located on the user's mouth side, air exhaled by the user is blown over the one of the at least two of the plurality of sheets, which one has higher gas permeability, from outside the space. In such a manner, a direction in which the gas stored in the space applies pressure faces a direction in which the air exhaled by the user applies pressure, that is, such a direction that the air exhaled by the user applies pressure to the space. Therefore, the air exhaled by the user wearing the gas storing mask is prevented from permeating the one of the at least two of the plurality of sheets, which one has higher gas permeability, and being mixed with the gas stored in the space.

The gas storing mask in accordance with an aspect of the present invention can be arranged such that: the plurality of sheets includes a first sheet and a second sheet; the first sheet is provided so as to face the second sheet and be located on a side of a living body wearing the gas storing mask; and the second sheet has gas permeability lower than that of the first sheet. According to the above configuration, the gas stored in the space formed between the first sheet and the second sheet easily permeates the first sheet and is easily discharged outside the space. Therefore, in a case where (i) the gas storing mask is worn by the user such that the first sheet is located on the user's (living body's) mouth side and (ii) the gas is supplied to the gas storing mask, the gas stored in the space easily permeates the first sheet and is easily supplied to the user. Furthermore, the gas stored in the space does not easily permeate the second sheet and does not easily leak out of the gas storing mask. Therefore, it is possible to efficiently provide, to the user, a gas therapy with use of the gas storing mask is used.

Moreover, according to the above configuration, in a case where the gas continues to be supplied to the space formed between the first sheet and the second sheet, a pressure of the gas stored in the space is increased. This causes the gas stored in the space to intend to permeate the first sheet and leak out of the space. Meanwhile, air exhaled by the user is blown over the first sheet from outside the space. In such a manner, a direction in which the gas stored in the space applies pressure faces a direction in which the air exhaled by the user applies pressure, that is, such a direction that the air exhaled by the user applies pressure to the space. Therefore, the air exhaled by the user wearing the gas storing mask is prevented from permeating the first sheet and being mixed with the gas stored in the space.

The gas storing mask in accordance with an aspect of the present invention can be arranged so as to further include: a gas supply pathway through which the gas is supplied to the gas storing mask, the gas supply pathway having at least one gas supply port; and a connecting part via which the at least one gas supply port is connected to at least one of the first sheet and the second sheet so as to be located between the first sheet and the second sheet. According to the above configuration, the at least one gas supply port is connected to at least one of the first sheet and the second sheet so as to be located between the first sheet and the second sheet. Accordingly, it is possible to absolutely store, between the first sheet and the second sheet, the gas supplied via the at least one gas supply port. This absolutely causes the gas supplied from outside the gas storing mask to permeate the first sheet and be supplied to the user. It is therefore possible to maintain more suitable humidity between the gas storing mask and the face of the user, and possible to more effectively provide, to the user, a gas therapy with use of the gas storing mask.

The gas storing mask in accordance with an aspect of the present invention can be arranged such that the connecting part is arranged such that the at least one gas supply port is located at a central portion of the first sheet. According to the above configuration, in a case where the gas is supplied from outside the gas storing mask, the space is formed, at the central portion of the first sheet, between adjacent ones of the plurality of sheets, and then expanded. Therefore, it is possible to store the gas, in a larger amount, in the space formed between the adjacent ones of the plurality of sheets. Accordingly, in a case where the gas storing mask is worn by the user, it is possible to provide a sufficient gas to the user from a vicinity of a central portion of the space which central portion faces a vicinity of the mouth of the user.

The gas storing mask in accordance with an aspect of the present invention can be arranged such that: the at least one gas supply port formed in the gas supply pathway includes a plurality of gas supply ports; and the connecting part is arranged such that the plurality of gas supply ports are located along a short side of the gas storing mask. According to the above configuration, the gas supply pathway is provided so as to extend along the short side of the gas storing mask. Therefore, in a case where the user wears the gas storing mask, the gas supply pathway is not easily noticeable in appearance. This allows the user to wear the gas storing mask without worrying about the public eye, as with the case of a conventional surgical mask.

The gas storing mask in accordance with an aspect of the present invention can be arranged such that the first sheet has at least one hole through which the gas stored in the space is supplied to the living body. According to the above configuration, the first sheet has the at least one hole. Therefore, in a case where the gas is supplied to the space formed between the first sheet and the second sheet, the gas is stored in the space, and the gas stored in the space intends to pass through the at least one hole formed in the first sheet and leak out of the space. Accordingly, the gas storing mask allows the gas to be more easily provided to the user (living body) wearing the gas storing mask. Moreover, a direction in which the user wearing the gas storing mask exhales faces a direction in which the gas stored in the space leaks. This makes it possible to absolutely prevent the air exhaled by the user from passing through the at least one hole formed in the first sheet and being mixed with the gas stored in the space.

The gas storing mask in accordance with an aspect of the present invention can be arranged such that: the plurality of sheets further includes a third sheet provided between the first sheet and the second sheet; the third sheet has gas permeability lower than that of the first sheet; and the third sheet has a hole through which the gas stored between the second sheet and the third sheet is introduced between the first sheet and the third sheet so as to permeate the first sheet.

According to the above configuration, the gas supplied from outside the gas storing mask is easily stored in the space formed between the second sheet and the third sheet each of which has gas permeability lower than that of the first sheet. Therefore, it is possible to prevent, in the space formed between the second sheet and the third sheet, a decrease in concentration of the gas supplied from outside the gas storing mask. Furthermore, according to the above configuration, the third sheet has the hole. This causes the gas stored in the space formed between the second sheet and the third sheet to easily pass through the hole formed in the third sheet and easily permeate the first sheet. Therefore, according to the gas storing mask, it is possible to easily provide the gas to the user wearing the gas storing mask.

Moreover, according to the above configuration, in a case where the gas continues to be supplied to the space formed between the first sheet and the third sheet, the gas stored in the space intends to pass through the hole formed in the third sheet and leak out of the space. Meanwhile a direction in which the user wearing the gas storing mask exhales faces a direction in which the gas stored in the space leaks. This makes it possible to absolutely prevent the air exhaled by the user from passing through the hole formed in the third sheet and being mixed with the gas stored in the space.

The gas storing mask in accordance with an aspect of the present invention can be arranged such that the second sheet has at least one hole through which air that has permeated the first sheet and has been stored in the space is discharged. According to the above configuration, the air (for example, air exhaled by the user) that has permeated the first sheet and has been stored between the first sheet and the second sheet passes through the at least one hole formed in the second sheet, and is discharged outside the gas storing mask. Therefore, it is possible to prevent, in the space formed between the first sheet and the second sheet, a decrease in concentration of the gas supplied from outside the gas storing mask.

The gas storing mask in accordance with an aspect of the present invention can be arranged such that the second sheet has the at least one hole at a central portion of the second sheet. According to the above configuration, in a case where the air (for example, air exhaled by the user) is blown over the first sheet, the air permeates the first sheet due to force of user's exhalation, passes through the at least one hole formed in the central portion of the second sheet, and is then discharged outside the gas storing mask. Such air blown over the first sheet causes the gas stored between the first sheet and the second sheet to flow so as to be away from the at least one hole. This causes the gas not to easily pass through the at least one hole and easily leak out of the space formed between the first sheet and the second sheet. Therefore, it is possible to prevent, in the space, a decrease in concentration of the gas supplied from outside the gas storing mask.

The gas storing mask in accordance with an aspect of the present invention can be arranged such that the second sheet has the at least one hole along a short side of the second sheet. According to the above configuration, in a case where the air (for example, air exhaled by the user) is blown over the first sheet, part of the air permeates the first sheet, passes through the at least one hole, and is then discharged outside the gas storing mask from the short side of the second sheet along having the at least one hole. Such air causes the gas stored between the first sheet and the second sheet to flow from a portion which is closer to the at least one hole to a portion which is farther from the at least one hole. This causes the gas not to easily pass through the at least one hole and easily leak out of the gas storing mask. Therefore, it is possible to prevent, in the space formed between the first sheet and the second sheet, a decrease in concentration of the gas supplied from outside the gas storing mask.

The gas storing mask in accordance with an aspect of the present invention can be arranged such that the gas permeability of the first sheet is arranged so as to be lower on a space side of the first sheet than on a living body side of the first sheet. According to the above configuration, the first sheet causes (i) the gas stored in the space formed between the first sheet and the second sheet to easily move out of the space and (ii) the air (for example, air exhaled by the user), blown over the first sheet from outside the space, not to easily enter the space. Therefore, in a case where the gas storing mask is worn by the user such that the first sheet is located on the user's mouth side, the gas stored in the space is easily supplied to the user, and the air exhaled by the user is not easily mixed with the gas stored in the space. It is therefore possible to efficiently provide, to the user, a gas therapy with use of the gas storing mask.

The gas storing mask in accordance with an aspect of the present invention can be arranged such that the gas permeates the first sheet and is stored in the space formed between the first sheet and the second sheet. According to the above configuration, it is not necessary to provide the gas supply pathway, through which the gas is supplied, between the first sheet and the second sheet. This makes it easy to provide the gas supply pathway to the gas storing mask.

The gas storing mask in accordance with an aspect of the present invention can be arranged such that: the plurality of sheets includes a/the first sheet and a/the second sheet; the gas storing mask further includes: a gas supply pathway through which the gas is supplied to the gas storing mask, the gas supply pathway having at least one gas supply port; and a connecting part via which the at least one gas supply port is connected to at least one of the first sheet and the second sheet so as to be located between the first sheet and the second sheet; and the connecting part is arranged such that the at least one gas supply port faces the first sheet.

According to the above configuration, the gas supplied via the at least one gas supply port is emitted toward the first sheet. Therefore, even in a case where the second sheet has gas permeability higher than that of the first sheet, the gas supplied via the at least one gas supply port permeates the first sheet more easily than the gas permeates the second sheet. Accordingly, in a case where the gas storing mask is worn by the user such that the first sheet is located on the user's mouth side, it is possible to efficiently provide, to the user, a therapy in which the gas storing mask is used.

INDUSTRIAL APPLICABILITY

The present invention is applicable to an oxygen therapy including a home oxygen therapy.

REFERENCE SIGNS LIST 1, 1a through 1k Oxygen delivering mask (gas storing mask)
2, 2a through 2c, 2k First sheet
3, 3a through 3d, 3i, 3k Second sheet
11 Mask body
12 Fiber sheet (first sheet)
13 Film sheet (second sheet)
4 Gas storing part
5, 5a through 5e Gas supply pathway
6 Gas supply port
7 Third sheet
71 through 73, 8, 8a, 81 Hole
15 Wearing part
16 Gas tube (gas supply pathway)
9, 9a, 9c Connecting part
9b Member (connecting part)

The invention claimed is:

1. A gas storing mask in which a gas is stored, the gas storing mask comprising:
a plurality of sheets including a first sheet and a second sheet;
the first sheet being provided so as to face the second sheet and be located on a side of a living body wearing the gas storing mask; and
the second sheet having gas permeability lower than that of the first sheet;
a gas supply pathway through which the gas is supplied from outside the gas storing mask, the gas supply pathway having at least one gas supply port; and
a connecting part via which the at least one gas supply port is connect to at least one of the first sheet and the second sheet so as to be located between the first sheet and the second sheet; and
the gas, which is supplied from the gas supply pathway, being stored in a space formed between the first sheet and the second sheet.

2. The gas storing mask as set forth in claim 1, wherein the first sheet and the second sheet are different from each other in gas permeability.

3. The gas storing mask as set forth in claim 1, wherein the connecting part is arranged such that the at least one gas supply port is located at a central portion of the first sheet.

4. The gas storing mask as set forth in claim 1, wherein:
the at least one gas supply port formed in the gas supply pathway includes a plurality of gas supply ports; and
the connecting part is arranged such that the plurality of gas supply ports are located along a short side of the gas storing mask.

5. The gas storing mask as set forth in claim 1, wherein the first sheet has at least one hole through which the gas stored in the space is supplied to the living body.

6. The gas storing mask as set forth in claim 1, wherein:
the plurality of sheets further includes a third sheet provided between the first sheet and the second sheet;
the third sheet has gas permeability lower than that of the first sheet; and
the third sheet has a hole through which the gas stored between the second sheet and the third sheet is introduced between the first sheet and the third sheet so as to permeate the first sheet.

7. The gas storing mask as set forth in claim 1, wherein the second sheet has at least one hole through which air that has permeated the first sheet and has been stored in the space is discharged.

8. The gas storing mask as set forth in claim 7, wherein the second sheet has the at least one hole at a central portion of the second sheet.

9. The gas storing mask as set forth in claim 7, wherein the second sheet has the at least one hole along a short side of the second sheet.

10. The gas storing mask as set forth in claim 1, wherein the gas permeability of the first sheet is arranged so as to be lower on a space side of the first sheet than on a living body side of the first sheet.

11. The gas storing mask as set forth in claim 1, wherein the gas permeates the first sheet and is stored in the space formed between the first sheet and the second sheet.

12. The gas storing mask as set forth in claim 1, wherein:
- the plurality of sheets includes a first sheet and a second sheet;
- the gas storing mask further comprises:
    - a gas supply pathway through which the gas is supplied to the gas storing mask, the gas supply pathway having at least one gas supply port; and
    - a connecting part via which the at least one gas supply port is connected to at least one of the first sheet and the second sheet so as to be located between the first sheet and the second sheet; and
- the connecting part is arranged such that the at least one gas supply port faces the first sheet.

* * * * *